United States Patent
Li et al.

(10) Patent No.: US 12,364,708 B2
(45) Date of Patent: Jul. 22, 2025

(54) INJECTABLE SCAFFOLD FOR TREATMENT OF INTRACRANIAL ANEURYSMS AND RELATED TECHNOLOGY

(71) Applicant: Covidien LP, Mansfield, MA (US)

(72) Inventors: Junwei Li, Irvine, CA (US); Gaurav Girdhar, Anaheim Hills, CA (US); John Wainwright, Foothill Ranch, CA (US); Yves Bayon, Autrans-Méaudre-en-Vercors (FR); Ariana Pagani, Huntington Beach, CA (US)

(73) Assignee: Covidien LP, Mansfield, MA (US)

( * ) Notice: Subject to any disclaimer, the term of this patent is extended or adjusted under 35 U.S.C. 154(b) by 37 days.

(21) Appl. No.: 18/483,809

(22) Filed: Oct. 10, 2023

(65) Prior Publication Data
US 2024/0033281 A1    Feb. 1, 2024

Related U.S. Application Data

(60) Continuation of application No. 16/669,978, filed on Oct. 31, 2019, now Pat. No. 11,813,282, which is a
(Continued)

(51) Int. Cl.
*A61K 31/722* (2006.01)
*A61B 17/12* (2006.01)
(Continued)

(52) U.S. Cl.
CPC ...... *A61K 31/722* (2013.01); *A61B 17/12031* (2013.01); *A61B 17/12113* (2013.01);
(Continued)

(58) Field of Classification Search
CPC ........ A61B 17/12031; A61B 17/12113; A61B 17/12181; A61B 17/12186; A61B 17/12195; A61L 2430/36
See application file for complete search history.

(56) References Cited

U.S. PATENT DOCUMENTS 5,041,090 A    8/1991    Scheglov et al.
5,250,071 A    10/1993    Palermo
(Continued)

FOREIGN PATENT DOCUMENTS

CA    3031482 A1    8/2017
CN    101460102 A    6/2009
(Continued)

OTHER PUBLICATIONS

Ashland, "Formulating Elegant Liquid and Semisolid Drug Products," Natrosol 250, Hydroxyethylcellulose (HEC), (2018) pp. 1-32 (Year: 2018).
(Continued)

*Primary Examiner* — Ashley L Fishback
(74) *Attorney, Agent, or Firm* — Fortem IP LLP

(57) ABSTRACT

A method for treating an aneurysm in accordance with a particular embodiment of the present technology includes intravascularly delivering a mixture including a biopolymer (e.g., chitosan) and a chemical crosslinking agent (e.g., genipin) to an aneurysm. The method further includes mixing the biopolymer and the chemical crosslinking agent to initiate chemical crosslinking of the biopolymer. The mixture is delivered to the aneurysm via a lumen and an exit port of a catheter while the chemical crosslinking is ongoing. The mixture exits the catheter as a single cohesive strand that at least partially agglomerates to form a mass occupying at least 75% of a total internal volume of the aneurysm. During delivery of the mixture, the method includes expanding a tubular flow diverter to reinforce a neck of the aneurysm.

20 Claims, 9 Drawing Sheets

Related U.S. Application Data division of application No. 15/299,929, filed on Oct. 21, 2016, now Pat. No. 10,576,099.

(51) Int. Cl.
*A61L 31/04* (2006.01)
*A61L 31/14* (2006.01)
*A61L 31/18* (2006.01)
*A61M 5/145* (2006.01)
*A61M 25/10* (2013.01)

(52) U.S. Cl.
CPC ...... *A61B 17/12186* (2013.01); *A61L 31/042* (2013.01); *A61L 31/145* (2013.01); *A61L 31/18* (2013.01); *A61M 5/1452* (2013.01); *A61M 25/10* (2013.01); *A61L 2400/06* (2013.01); *A61L 2430/36* (2013.01); *A61M 2210/0687* (2013.01)

(56) References Cited

U.S. PATENT DOCUMENTS

| | | |
|---|---|---|
| 5,261,916 A | 11/1993 | Engelson |
| 5,284,488 A | 2/1994 | Sideris |
| 5,326,350 A | 7/1994 | Li |
| 5,354,295 A | 10/1994 | Guglielmi et al. |
| 5,405,379 A | 4/1995 | Lane |
| 5,417,708 A | 5/1995 | Hall et al. |
| 5,601,600 A | 2/1997 | Ton |
| 5,645,558 A | 7/1997 | Horton |
| 5,669,931 A | 9/1997 | Kupiecki et al. |
| 5,725,552 A | 3/1998 | Kotula et al. |
| 5,733,294 A | 3/1998 | Forber et al. |
| 5,741,333 A | 4/1998 | Frid |
| 5,749,891 A | 5/1998 | Ken et al. |
| 5,749,894 A | 5/1998 | Engelson |
| 5,749,895 A | 5/1998 | Sawyer et al. |
| 5,749,919 A | 5/1998 | Blanc |
| 5,814,062 A | 9/1998 | Sepetka et al. |
| 5,823,198 A | 10/1998 | Jones et al. |
| 5,846,261 A | 12/1998 | Kotula et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,941,249 A | 8/1999 | Maynard |
| 5,944,738 A | 8/1999 | Amplatz et al. |
| 5,951,599 A | 9/1999 | McCrory |
| 5,964,797 A | 10/1999 | Ho |
| 5,976,169 A | 11/1999 | Imran |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Mllar et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz |
| 6,139,564 A | 10/2000 | Teoh |
| 6,152,144 A | 11/2000 | Lesh et al. |
| 6,159,531 A | 12/2000 | Dang et al. |
| 6,165,193 A | 12/2000 | Greene et al. |
| 6,168,615 B1 | 1/2001 | Ken et al. |
| 6,168,622 B1 | 1/2001 | Mazzocchi |
| 6,238,403 B1 | 5/2001 | Greene et al. |
| 6,299,619 B1 | 10/2001 | Greene et al. |
| 6,309,367 B1 | 10/2001 | Boock |
| 6,322,576 B1 | 11/2001 | Wallace et al. |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz |
| 6,371,980 B1 | 4/2002 | Rudakov et al. |
| 6,375,668 B1 | 4/2002 | Gifford et al. |
| 6,379,329 B1 | 4/2002 | Naglreiter et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van et al. |
| 6,569,179 B2 | 5/2003 | Teoh et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,591,472 B1 | 7/2003 | Noone et al. |
| 6,592,605 B2 | 7/2003 | Lenker et al. |
| 6,599,308 B2 | 7/2003 | Amplatz |
| 6,602,261 B2 | 8/2003 | Greene et al. |
| 6,605,101 B1 | 8/2003 | Schaefer et al. |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,555 B1 | 11/2003 | Vantassel et al. |
| 6,652,556 B1 | 11/2003 | Vantassel et al. |
| 6,666,882 B1 | 12/2003 | Bose et al. |
| 6,669,717 B2 | 12/2003 | Marotta et al. |
| 6,669,721 B1 | 12/2003 | Bose et al. |
| 6,682,546 B2 | 1/2004 | Amplatz |
| 6,689,150 B1 | 2/2004 | Vantassel et al. |
| 6,689,486 B2 | 2/2004 | Ho et al. |
| 6,723,112 B2 | 4/2004 | Ho et al. |
| 6,723,116 B2 | 4/2004 | Taheri |
| 6,730,108 B2 | 5/2004 | Van et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,905,503 B2 | 6/2005 | Gifford et al. |
| 6,936,055 B1 | 8/2005 | Ken et al. |
| 6,936,058 B2 | 8/2005 | Forde et al. |
| 6,949,113 B2 | 9/2005 | Van et al. |
| 6,953,473 B2 | 10/2005 | Porter |
| 6,991,617 B2 | 1/2006 | Hektner et al. |
| 6,994,092 B2 | 2/2006 | Van et al. |
| 6,994,717 B2 | 2/2006 | Konya et al. |
| 7,011,671 B2 | 3/2006 | Welch |
| 7,014,645 B2 | 3/2006 | Greene et al. |
| 7,029,487 B2 | 4/2006 | Greene et al. |
| 7,029,949 B2 | 4/2006 | Farnworth et al. |
| 7,070,609 B2 | 7/2006 | West |
| 7,083,632 B2 | 8/2006 | Avellanet et al. |
| 7,098,194 B2 | 8/2006 | Chenite et al. |
| 7,128,073 B1 | 10/2006 | Van et al. |
| 7,128,736 B1 | 10/2006 | Abrams et al. |
| 7,153,323 B1 | 12/2006 | Teoh et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,306,622 B2 | 12/2007 | Jones et al. |
| 7,326,225 B2 | 2/2008 | Ferrera et al. |
| 7,331,980 B2 | 2/2008 | Dubrul et al. |
| 7,367,986 B2 | 5/2008 | Mazzocchi et al. |
| 7,410,482 B2 | 8/2008 | Murphy et al. |
| 7,419,503 B2 | 9/2008 | Pulnev et al. |
| 7,473,266 B2 | 1/2009 | Glaser |
| 7,481,821 B2 | 1/2009 | Fogarty et al. |

(56) References Cited

U.S. PATENT DOCUMENTS

| | | |
|---|---|---|
| 7,491,214 B2 | 2/2009 | Greene et al. |
| 7,569,066 B2 | 8/2009 | Gerberding et al. |
| 7,572,288 B2 | 8/2009 | Cox |
| 7,597,704 B2 | 10/2009 | Frazier et al. |
| 7,601,160 B2 | 10/2009 | Richter |
| 7,608,088 B2 | 10/2009 | Jones et al. |
| 7,695,488 B2 | 4/2010 | Berenstein et al. |
| 7,699,056 B2 | 4/2010 | Tran et al. |
| 7,708,754 B2 | 5/2010 | Balgobin et al. |
| 7,727,189 B2 | 6/2010 | Vantassel et al. |
| 7,744,583 B2 | 6/2010 | Seifert et al. |
| 7,744,652 B2 | 6/2010 | Morsi |
| 7,799,767 B2 | 9/2010 | Lamberti et al. |
| 7,879,065 B2 | 2/2011 | Gesswein et al. |
| 7,976,527 B2 | 7/2011 | Cragg et al. |
| RE42,625 E | 8/2011 | Guglielmi |
| 7,993,364 B2 | 8/2011 | Morsi |
| RE42,758 E | 9/2011 | Ken et al. |
| 8,012,210 B2 | 9/2011 | Lin et al. |
| 8,043,326 B2 | 10/2011 | Hancock et al. |
| 8,062,379 B2 | 11/2011 | Morsi |
| 8,075,585 B2 | 12/2011 | Lee et al. |
| 8,137,293 B2 | 3/2012 | Zhou et al. |
| 8,142,456 B2 | 3/2012 | Rosqueta et al. |
| 8,153,612 B2 | 4/2012 | Ben-Shalom et al. |
| 8,202,280 B2 | 6/2012 | Richter |
| 8,211,160 B2 | 7/2012 | Garrison et al. |
| 8,221,445 B2 | 7/2012 | Van et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,372,062 B2 | 2/2013 | Murphy et al. |
| 8,398,670 B2 | 3/2013 | Amplatz et al. |
| 8,425,541 B2 | 4/2013 | Masters et al. |
| 8,470,013 B2 | 6/2013 | Duggal et al. |
| 8,530,632 B2 | 9/2013 | Tijsma et al. |
| 8,597,320 B2 | 12/2013 | Sepetka et al. |
| 8,603,128 B2 | 12/2013 | Greene et al. |
| 8,653,319 B2 | 2/2014 | Amery et al. |
| 8,690,936 B2 | 4/2014 | Nguyen et al. |
| 8,715,317 B1 | 5/2014 | Janardhan et al. |
| 8,809,301 B2 | 8/2014 | Athanasiadis et al. |
| 8,834,515 B2 | 9/2014 | Win et al. |
| 8,840,867 B2 | 9/2014 | Sophie et al. |
| 8,906,057 B2 | 12/2014 | Connor et al. |
| 8,974,512 B2 | 3/2015 | Aboytes et al. |
| 8,998,947 B2 | 4/2015 | Aboytes et al. |
| 9,034,348 B2 | 5/2015 | Ben-Shalom et al. |
| 9,192,574 B2 | 11/2015 | Medina et al. |
| 9,192,692 B2 | 11/2015 | Medina et al. |
| 9,211,202 B2 | 12/2015 | Strother et al. |
| 9,301,769 B2 | 4/2016 | Brady et al. |
| 9,314,248 B2 | 4/2016 | Molaei |
| 9,333,220 B2 | 5/2016 | Tijsma et al. |
| 9,339,275 B2 | 5/2016 | Trommeter et al. |
| 9,433,636 B2 | 9/2016 | Tijsma et al. |
| 9,486,224 B2 | 11/2016 | Riina et al. |
| 9,555,120 B2 | 1/2017 | Andersson |
| 9,629,636 B2 | 4/2017 | Fogarty et al. |
| 9,655,842 B1 | 5/2017 | Girdhar et al. |
| 9,681,861 B2 | 6/2017 | Heisel et al. |
| 9,700,648 B2 | 7/2017 | Hissong et al. |
| 9,713,475 B2 | 7/2017 | Divino et al. |
| 9,731,043 B2 | 8/2017 | Lerouge et al. |
| 9,833,309 B2 | 12/2017 | Levi et al. |
| 9,844,380 B2 | 12/2017 | Furey |
| 9,901,543 B2 | 2/2018 | Chausson et al. |
| 9,907,684 B2 | 3/2018 | Connor et al. |
| 9,918,718 B2 | 3/2018 | Lorenzo |
| 9,925,210 B2 | 3/2018 | McCarthy et al. |
| 9,962,146 B2 | 5/2018 | Hebert et al. |
| 10,028,745 B2 | 7/2018 | Morsi |
| 10,130,372 B2 | 11/2018 | Griffin |
| 10,517,986 B2 | 12/2019 | Sherman et al. |
| 10,576,099 B2 | 3/2020 | Li et al. |
| 10,632,143 B2 | 4/2020 | McCarthy et al. |
| 10,932,933 B2 | 3/2021 | Bardsley et al. |
| 10,952,740 B2 | 3/2021 | Dasnurkar et al. |
| 11,076,860 B2 | 8/2021 | Lorenzo |
| 11,134,953 B2 | 10/2021 | Solaun |
| 11,179,159 B2 | 11/2021 | Cox et al. |
| 11,389,309 B2 | 7/2022 | Ruvalcaba et al. |
| 11,504,816 B2 | 11/2022 | Nguyen et al. |
| 11,679,458 B2 | 6/2023 | Nguyen et al. |
| 11,685,007 B2 | 6/2023 | Li et al. |
| 11,690,628 B2 | 7/2023 | Divino et al. |
| 11,717,924 B2 | 8/2023 | Nguyen et al. |
| 11,813,282 B2 | 11/2023 | Li et al. |
| 12,256,936 B2 | 3/2025 | Li et al. |
| 2001/0000797 A1 | 5/2001 | Mazzocchi |
| 2001/0001835 A1 | 5/2001 | Greene et al. |
| 2002/0026210 A1 | 2/2002 | Abdel-Gawwad |
| 2002/0042628 A1 | 4/2002 | Chin et al. |
| 2002/0062145 A1 | 5/2002 | Rudakov et al. |
| 2002/0119177 A1 | 8/2002 | Bowman et al. |
| 2002/0147462 A1 | 10/2002 | Mair et al. |
| 2002/0165572 A1 | 11/2002 | Saadat |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0065303 A1 | 4/2003 | Wellman et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2003/0149490 A1 | 8/2003 | Ashman |
| 2003/0171739 A1 | 9/2003 | Murphy et al. |
| 2003/0187473 A1 | 10/2003 | Berenstein et al. |
| 2003/0195553 A1 | 10/2003 | Wallace et al. |
| 2003/0212419 A1 | 11/2003 | West |
| 2004/0034386 A1 | 2/2004 | Fulton et al. |
| 2004/0044361 A1 | 3/2004 | Frazier et al. |
| 2004/0044391 A1 | 3/2004 | Porter |
| 2004/0064093 A1 | 4/2004 | Hektner et al. |
| 2004/0098027 A1 | 5/2004 | Teoh et al. |
| 2004/0106945 A1 | 6/2004 | Thramann et al. |
| 2004/0115164 A1 | 6/2004 | Pierce et al. |
| 2004/0122467 A1 | 6/2004 | Vantassel et al. |
| 2004/0133222 A1 | 7/2004 | Tran et al. |
| 2004/0138758 A1 | 7/2004 | Kronengold et al. |
| 2004/0161451 A1 | 8/2004 | Pierce et al. |
| 2004/0167597 A1 | 8/2004 | Costantino et al. |
| 2004/0176798 A1 | 9/2004 | Foy et al. |
| 2004/0181253 A1 | 9/2004 | Sepetka et al. |
| 2004/0236344 A1 | 11/2004 | Monstadt et al. |
| 2005/0021077 A1 | 1/2005 | Chin et al. |
| 2005/0038470 A1 | 2/2005 | Van et al. |
| 2005/0049625 A1 | 3/2005 | Shaya et al. |
| 2005/0089554 A1 | 4/2005 | Cormier et al. |
| 2005/0119684 A1 | 6/2005 | Guterman et al. |
| 2005/0131443 A1 | 6/2005 | Abdel-Gawwad |
| 2005/0222580 A1 | 10/2005 | Gifford et al. |
| 2005/0267510 A1 | 12/2005 | Razack |
| 2005/0267511 A1 | 12/2005 | Marks et al. |
| 2005/0267527 A1 | 12/2005 | Sandoval et al. |
| 2005/0277978 A1 | 12/2005 | Greenhalgh |
| 2005/0278023 A1 | 12/2005 | Zwirkoski |
| 2006/0028209 A1 | 2/2006 | Walker |
| 2006/0034883 A1 | 2/2006 | Dang et al. |
| 2006/0052816 A1 | 3/2006 | Bates et al. |
| 2006/0064151 A1 | 3/2006 | Guterman et al. |
| 2006/0106421 A1 | 5/2006 | Teoh |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0122548 A1 | 6/2006 | Abrams |
| 2006/0155323 A1 | 7/2006 | Porter et al. |

(56) References Cited

U.S. PATENT DOCUMENTS

| | | |
|---|---|---|
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2006/0276824 A1 | 12/2006 | Mitelberg et al. |
| 2006/0276829 A1 | 12/2006 | Balgobin et al. |
| 2006/0276830 A1 | 12/2006 | Balgobin et al. |
| 2007/0003594 A1 | 1/2007 | Brady et al. |
| 2007/0010850 A1 | 1/2007 | Balgobin et al. |
| 2007/0014831 A1 | 1/2007 | Sung et al. |
| 2007/0083226 A1 | 4/2007 | Buiser et al. |
| 2007/0100426 A1 | 5/2007 | Rudakov et al. |
| 2007/0135907 A1 | 6/2007 | Wilson et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179507 A1 | 8/2007 | Shah |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0186933 A1 | 8/2007 | Domingo et al. |
| 2007/0191924 A1 | 8/2007 | Rudakov |
| 2007/0198059 A1 | 8/2007 | Patel et al. |
| 2007/0198075 A1 | 8/2007 | Levy |
| 2007/0219619 A1 | 9/2007 | Dieck et al. |
| 2007/0221230 A1 | 9/2007 | Thompson et al. |
| 2007/0265656 A1 | 11/2007 | Amplatz et al. |
| 2007/0270902 A1 | 11/2007 | Slazas et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2007/0299461 A1 | 12/2007 | Elliott |
| 2008/0033366 A1 | 2/2008 | Matson et al. |
| 2008/0065145 A1 | 3/2008 | Carpenter |
| 2008/0069801 A1 | 3/2008 | Lee et al. |
| 2008/0081763 A1 | 4/2008 | Swetlin et al. |
| 2008/0082176 A1 | 4/2008 | Slazas |
| 2008/0086196 A1 | 4/2008 | Truckai et al. |
| 2008/0109057 A1 | 5/2008 | Calabria et al. |
| 2008/0114391 A1 | 5/2008 | Dieck et al. |
| 2008/0114436 A1 | 5/2008 | Dieck et al. |
| 2008/0119886 A1 | 5/2008 | Greenhalgh et al. |
| 2008/0125852 A1 | 5/2008 | Garrison et al. |
| 2008/0132820 A1 | 6/2008 | Buckman et al. |
| 2008/0140177 A1 | 6/2008 | Hines |
| 2008/0195137 A1 | 8/2008 | Alleyne et al. |
| 2008/0200945 A1 | 8/2008 | Amplatz et al. |
| 2008/0200979 A1 | 8/2008 | Dieck et al. |
| 2008/0221554 A1 | 9/2008 | OConnor et al. |
| 2008/0221600 A1 | 9/2008 | Dieck et al. |
| 2008/0221703 A1 | 9/2008 | Que et al. |
| 2008/0281350 A1 | 11/2008 | Sepetka et al. |
| 2008/0283066 A1 | 11/2008 | Delgado et al. |
| 2009/0018637 A1 | 1/2009 | Paul et al. |
| 2009/0024224 A1 | 1/2009 | Chen et al. |
| 2009/0025820 A1 | 1/2009 | Adams |
| 2009/0036877 A1 | 2/2009 | Nardone et al. |
| 2009/0043375 A1 | 2/2009 | Rudakov et al. |
| 2009/0056722 A1 | 3/2009 | Swann |
| 2009/0062899 A1 | 3/2009 | Dang et al. |
| 2009/0076540 A1 | 3/2009 | Marks et al. |
| 2009/0099592 A1 | 4/2009 | Buiser et al. |
| 2009/0112249 A1 | 4/2009 | Miles et al. |
| 2009/0112251 A1 | 4/2009 | Qian et al. |
| 2009/0125119 A1 | 5/2009 | Obermiller et al. |
| 2009/0148492 A1 | 6/2009 | Dave et al. |
| 2009/0155367 A1 | 6/2009 | Neuwirth et al. |
| 2009/0187214 A1 | 7/2009 | Amplatz et al. |
| 2009/0264978 A1 | 10/2009 | Dieck et al. |
| 2009/0270974 A1 | 10/2009 | Berez et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0287297 A1 | 11/2009 | Cox |
| 2009/0297582 A1 | 12/2009 | Meyer et al. |
| 2009/0306702 A1 | 12/2009 | Miloslavski et al. |
| 2009/0306706 A1 | 12/2009 | Osypka |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0021545 A1 | 1/2010 | Chaput et al. |
| 2010/0023046 A1 | 1/2010 | Heidner et al. |
| 2010/0023048 A1 | 1/2010 | Mach |
| 2010/0030200 A1 | 2/2010 | Strauss et al. |
| 2010/0036410 A1 | 2/2010 | Krolik et al. |
| 2010/0106178 A1 | 4/2010 | Obermiller et al. |
| 2010/0121350 A1 | 5/2010 | Mirigian |
| 2010/0131002 A1 | 5/2010 | Connor et al. |
| 2010/0139465 A1 | 6/2010 | Christian et al. |
| 2010/0144895 A1 | 6/2010 | Porter |
| 2010/0160949 A1 | 6/2010 | Takuma |
| 2010/0174269 A1 | 7/2010 | Tompkins et al. |
| 2010/0184720 A1 | 7/2010 | Gavard et al. |
| 2010/0185271 A1 | 7/2010 | Zhang |
| 2010/0228184 A1 | 9/2010 | Mavani et al. |
| 2010/0249830 A1 | 9/2010 | Nelson |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2010/0274276 A1 | 10/2010 | Chow et al. |
| 2010/0298791 A1 | 11/2010 | Jones et al. |
| 2010/0312061 A1 | 12/2010 | Hess et al. |
| 2011/0022149 A1 | 1/2011 | Cox et al. |
| 2011/0046658 A1 | 2/2011 | Connor et al. |
| 2011/0077620 A1 | 3/2011 | Debeer |
| 2011/0125110 A1 | 5/2011 | Cotton |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0166588 A1 | 7/2011 | Connor et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0238041 A1 | 9/2011 | Lim et al. |
| 2011/0245862 A1 | 10/2011 | Dieck et al. |
| 2011/0251699 A1 | 10/2011 | Ladet |
| 2011/0265943 A1 | 11/2011 | Rosqueta et al. |
| 2011/0319926 A1 | 12/2011 | Becking et al. |
| 2012/0010644 A1 | 1/2012 | Sideris et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0123510 A1 | 5/2012 | Liungman |
| 2012/0143237 A1 | 6/2012 | Cam et al. |
| 2012/0143243 A1 | 6/2012 | Hill et al. |
| 2012/0143301 A1 | 6/2012 | Maslanka et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0271344 A1 | 10/2012 | Ford et al. |
| 2012/0283768 A1 | 11/2012 | Cox et al. |
| 2012/0283769 A1 | 11/2012 | Cruise et al. |
| 2012/0310269 A1 | 12/2012 | Fearnot et al. |
| 2012/0316598 A1 | 12/2012 | Becking et al. |
| 2012/0316632 A1 | 12/2012 | Gao |

(56) References Cited

U.S. PATENT DOCUMENTS

| | | |
|---|---|---|
| 2012/0323271 A1 | 12/2012 | Obermiller et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0073026 A1 | 3/2013 | Russo et al. |
| 2013/0085522 A1 | 4/2013 | Becking et al. |
| 2013/0116722 A1 | 5/2013 | Aboytes et al. |
| 2013/0138136 A1 | 5/2013 | Beckham et al. |
| 2013/0211495 A1 | 8/2013 | Halden et al. |
| 2013/0244972 A1 | 9/2013 | Ben-Shalom et al. |
| 2013/0274866 A1 | 10/2013 | Cox et al. |
| 2014/0012307 A1 | 1/2014 | Franano et al. |
| 2014/0017210 A1 | 1/2014 | Laurencin et al. |
| 2014/0039542 A1 | 2/2014 | Trommeter et al. |
| 2014/0058420 A1 | 2/2014 | Hannes et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0200607 A1 | 7/2014 | Sepetka et al. |
| 2014/0215792 A1 | 8/2014 | Leopold et al. |
| 2014/0257360 A1 | 9/2014 | Keillor |
| 2014/0257361 A1 | 9/2014 | Prom |
| 2014/0257374 A1 | 9/2014 | Heisel et al. |
| 2014/0316012 A1 | 10/2014 | Freyman et al. |
| 2014/0371734 A1 | 12/2014 | Truckai |
| 2014/0377187 A1 | 12/2014 | Lerouge et al. |
| 2015/0005808 A1 | 1/2015 | Chouinard et al. |
| 2015/0133989 A1 | 5/2015 | Lubock et al. |
| 2015/0216684 A1 | 8/2015 | Enzmann et al. |
| 2015/0250628 A1 | 9/2015 | Monstadt et al. |
| 2015/0272589 A1 | 10/2015 | Lorenzo |
| 2015/0272590 A1 | 10/2015 | Aboytes et al. |
| 2015/0313605 A1 | 11/2015 | Griffin |
| 2015/0313737 A1 | 11/2015 | Tippett et al. |
| 2015/0327843 A1 | 11/2015 | Garrison |
| 2015/0335333 A1 | 11/2015 | Jones et al. |
| 2015/0342613 A1 | 12/2015 | Aboytes et al. |
| 2015/0343181 A1 | 12/2015 | Bradway et al. |
| 2016/0022445 A1 | 1/2016 | Ruvalcaba et al. |
| 2016/0030050 A1 | 2/2016 | Franano et al. |
| 2016/0066921 A1 | 3/2016 | Seifert et al. |
| 2016/0082037 A1 | 3/2016 | Kirsch et al. |
| 2016/0106437 A1 | 4/2016 | Van Der Burg et al. |
| 2016/0128699 A1 | 5/2016 | Hadley et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0249935 A1 | 9/2016 | Hewitt et al. |
| 2016/0256170 A1 | 9/2016 | Busold et al. |
| 2016/0296714 A1 | 10/2016 | Mide et al. |
| 2016/0331381 A1 | 11/2016 | Ma |
| 2017/0105739 A1 | 4/2017 | Dias et al. |
| 2017/0150971 A1 | 6/2017 | Hines |
| 2017/0156734 A1 | 6/2017 | Griffin |
| 2017/0156903 A1 | 6/2017 | Shobayashi |
| 2017/0189035 A1 | 7/2017 | Porter |
| 2017/0224350 A1 | 8/2017 | Shimizu et al. |
| 2017/0224355 A1 | 8/2017 | Bowman et al. |
| 2017/0246340 A1 | 8/2017 | Girdhar |
| 2017/0266023 A1 | 9/2017 | Thomas |
| 2017/0296466 A1 | 10/2017 | Girdhar et al. |
| 2017/0312364 A1 | 11/2017 | Bossy et al. |
| 2017/0340333 A1 | 11/2017 | Badruddin et al. |
| 2017/0354419 A1 | 12/2017 | Teoh et al. |
| 2017/0354421 A1 | 12/2017 | Maguire et al. |
| 2017/0367708 A1 | 12/2017 | Mayer et al. |
| 2017/0367713 A1 | 12/2017 | Greene et al. |
| 2018/0049859 A1 | 2/2018 | Stoppenhagen et al. |
| 2018/0070955 A1 | 3/2018 | Greene et al. |
| 2018/0110797 A1 | 4/2018 | Li et al. |
| 2018/0125686 A1 | 5/2018 | Lu |
| 2018/0132856 A1 | 5/2018 | Wierzbicki et al. |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2018/0242979 A1 | 8/2018 | Lorenzo |
| 2018/0256171 A1 | 9/2018 | Chow et al. |
| 2018/0317932 A1 | 11/2018 | H'Doubler |
| 2019/0008522 A1 | 1/2019 | Lorenzo |
| 2019/0009057 A1 | 1/2019 | Li et al. |
| 2019/0053807 A1 | 2/2019 | Tassoni et al. |
| 2019/0053811 A1 | 2/2019 | Garza et al. |
| 2019/0223876 A1 | 7/2019 | Badruddin et al. |
| 2019/0223881 A1 | 7/2019 | Hewitt et al. |
| 2019/0282242 A1 | 9/2019 | Divino et al. |
| 2019/0343532 A1 | 11/2019 | Divino et al. |
| 2019/0351107 A1 | 11/2019 | Sawhney et al. |
| 2020/0060965 A1 | 2/2020 | Supper |
| 2020/0061099 A1 | 2/2020 | Li et al. |
| 2020/0113576 A1 | 4/2020 | Gorochow et al. |
| 2020/0138448 A1 | 5/2020 | Dasnurkar et al. |
| 2020/0268392 A1 | 8/2020 | Choi et al. |
| 2020/0315644 A1 | 10/2020 | Bowman |
| 2020/0360419 A1 | 11/2020 | McCarthy et al. |
| 2021/0022743 A1 | 1/2021 | Delaney et al. |
| 2021/0128160 A1 | 5/2021 | Li et al. |
| 2021/0128161 A1 | 5/2021 | Nageswaran et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0137530 A1 | 5/2021 | Greene et al. |
| 2021/0153872 A1 | 5/2021 | Nguyen et al. |
| 2021/0161643 A1 | 6/2021 | Totten et al. |
| 2021/0196284 A1 | 7/2021 | Gorochow et al. |
| 2021/0212698 A1 | 7/2021 | Connor |
| 2022/0008082 A1 | 1/2022 | Connor |
| 2022/0296788 A1 | 9/2022 | Hussain et al. |
| 2022/0304696 A2 | 9/2022 | Rhee et al. |
| 2023/0023511 A1 | 1/2023 | Nguyen et al. |
| 2023/0294223 A1 | 9/2023 | Li et al. |
| 2023/0311254 A1 | 10/2023 | Nguyen et al. |
| 2023/0373040 A1 | 11/2023 | Nguyen et al. |
| 2024/0050099 A1 | 2/2024 | Pecor et al. |

FOREIGN PATENT DOCUMENTS

| | | |
|---|---|---|
| CN | 102083493 A | 6/2011 |
| CN | 102202585 A | 9/2011 |
| CN | 202313544 U | 7/2012 |
| CN | 102740799 A | 10/2012 |
| CN | 105105812 A | 12/2015 |
| CN | 105209075 A | 12/2015 |
| DE | 102011102933 A1 | 12/2012 |
| EP | 0717969 A2 | 6/1996 |
| EP | 1188414 A1 | 3/2002 |
| EP | 1813213 A2 | 8/2007 |
| EP | 2208483 A1 | 7/2010 |
| EP | 1448607 B1 | 1/2011 |
| EP | 2566454 B1 | 3/2014 |
| EP | 2468348 B1 | 10/2016 |
| EP | 2121026 B1 | 6/2017 |
| JP | 2005261951 A | 9/2005 |
| JP | 2008521492 A | 6/2008 |
| WO | 9406502 A2 | 3/1994 |
| WO | 9905977 A1 | 2/1999 |
| WO | 03011151 A1 | 2/2003 |
| WO | 2006034149 A2 | 3/2006 |
| WO | 2007006139 A1 | 1/2007 |
| WO | 2007079402 A2 | 7/2007 |
| WO | 2007121405 A2 | 10/2007 |
| WO | 2008074027 A1 | 6/2008 |
| WO | 2009014528 A1 | 1/2009 |
| WO | 2009134337 A1 | 11/2009 |
| WO | 2010009019 A1 | 1/2010 |
| WO | 2010027363 A1 | 3/2010 |
| WO | 2010028300 A1 | 3/2010 |
| WO | 2010077599 A1 | 7/2010 |

(56) References Cited

FOREIGN PATENT DOCUMENTS

| | | | |
|---|---|---|---|
| WO | 2011066962 A1 | 6/2011 |
| WO | 2011095966 A1 | 8/2011 |
| WO | 2012034135 A1 | 3/2012 |
| WO | 2013112944 A1 | 8/2013 |
| WO | 2013138615 A2 | 9/2013 |
| WO | 2013138615 A3 | 9/2014 |
| WO | 2014169708 A1 | 10/2014 |
| WO | 2015160721 A1 | 10/2015 |
| WO | 2015166013 A1 | 11/2015 |
| WO | 2016098057 A1 | 6/2016 |
| WO | 2017074411 A1 | 5/2017 |
| WO | 2018050262 A1 | 3/2018 |
| WO | 2018051187 A1 | 3/2018 |
| WO | 2019038293 A1 | 2/2019 |
| WO | 2020162764 A1 | 8/2020 |
| WO | 2020236917 A1 | 11/2020 |
| WO | 2020262817 A1 | 12/2020 |
| WO | 2021046389 A1 | 3/2021 |

OTHER PUBLICATIONS

Fawal, Gomaa F. El, "Hydroxyethyl Cellulose Hydrogel for Wound Dressing: Fabrication Characterization and in Vitro Evaluation," International Journal of Biological Macromolecules 111 (2018); pp. 649-659 (Year: 2018).

Naderi-Meshkin, Hojjat, et al., "Chitosan-Based Injectable Hydrogel as a Promising in Situ Forming Scaffold for Cartilage Tissue Engineering," Cell Biol Int 38 (2014) pp. 72-84 (Year: 2014).

Medtronic ENT. (2021). Discover Novapak: Beyond Structural Stability [Brochure]. Medtronic.

Barnett, et al., "Assessment of EmboGel—A Selectively Dissolvable Radiopaque Hydrogel for Embolic Applications", J Vasc Interv Radiol 2011; vol. 22, No. 2, Feb. 2011, pp. 203-211.

Berenstein, et al., "Treatment of Experimental Aneurysms With an Embolic-Containing Device and Liquid Embolic Agent: Feasibility and Angiographic and Histological Results", Neurosurgery, vol. 64, No. 2, Feb. 2009, pp. 367-373.

Brennecka, et al., "In vivo embolization of lateral wall aneurysms in canines using the liquid-to-solid gelling PPODA-QT polymer system: 6-month pilot study", Laboratory investigation, J Neurosurg, vol. 119,, Jul. 2013, pp. 228-238.

Coutu, Jean-Michel, et al., "A new radiopaque embolizing agent for the treatment of endoleaks after endovascular repair: Influence of contrast agent on chitosan thermogel properties", Journal of Biomedical Materials Research Part B: Applied Biomaterials, 101B(1), 153-161. https://doi.org/10.1002/jbm.b.32828.

Jalani, et al., "Tough, In-Situ Thermogelling, Injectable Hydrogels for Biomedical Applications", Macromolecular Bioscience, 2014, 8 Pages.

Murayama, et al., "Endovascular Treatment of Experimental Aneurysms by Use of a Combination of Liquid Embolic Agents and Protective Devices", Experimental Aneurysms, AJNR Am J Neuroradiol, vol. 21, Oct. 2000, pp. 1726-1735.

Ning, et al., "Experimental study of temperature-sensitive chitosan/β-glycerophosphate embolic material in embolizing the basicranial rete mirabile in swines", Experimental and Therapeutic Medicine, vol. 10, Feb. 19, 2015, pp. 316-322.

Shive, Matthew S., et al., "BST-Cargel® treatment maintains cartilage repair superiority over microfracture at 5 years in a multicenter randomized controlled trial.", Cartilage, 6(2), 62-72. https://doi.org/10.1177/1947603514562064.

Supper, Stephanie, et al., "Chitosan/glucose 1-phosphate as new stable in situ forming depot system for controlled drug delivery", European Journal of Pharmaceutics and Biopharmaceutics, 88(2), 361-373. https://doi.org/10.1016/j.ejpb.2014.05.015.

Supper, Stephanie, et al., "Rheological Study of Chitosan/Polyolphosphate Systems: Influence of the Polyol Part on the Thermo-Induced Gelation Mechanism", Langmuir, 29(32), 10229-10237. https://doi.org/10.1021/la401993q.

Wang, et al., "In Vivo Assessment of Chitosan/β-Glycerophosphate as a New Liquid Embolic Agent", Interventional Neuroradiology, vol. 17, 2011, pp. 87-92.

Zhen, et al., "Embolization of aneurysm by chitosan-glycerophosphate-fibroblast tissue hydrogel, a tissue engineering material: experiment with rabbits", Natl Med J China, vol. 89, No. 11, Mar. 24, 2009, pp. 727-731.

INJECTABLE SCAFFOLD FOR TREATMENT OF INTRACRANIAL ANEURYSMS AND RELATED TECHNOLOGY

CROSS-REFERENCE TO RELATED APPLICATION(S)

This application is a continuation of U.S. patent application Ser. No. 16/669,978, filed Oct. 31, 2019, which is a divisional of U.S. patent application Ser. No. 15/299,929, filed Oct. 21, 2016, now U.S. Pat. No. 10,576,099, the disclosure each of which is incorporated herein by reference in its entirety.

TECHNICAL FIELD

The present technology is related to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs.

For these and other reasons, there is a need for innovation in the treatment of intracranial aneurysms. Given the severity of this condition, innovation in this field has immediate life-saving potential.

SUMMARY

Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1, Clause 13, or Clause 22.

1. A method for treating an aneurysm, the method comprising:
   intravascularly advancing a catheter toward an aneurysm at a portion of a blood vessel, wherein the catheter includes an elongate lumen and an exit port at a distal end portion of the lumen;
   mixing a biopolymer and a chemical crosslinking agent to initiate chemical crosslinking of the biopolymer;
   flowing the biopolymer and the chemical crosslinking agent toward an internal volume of the aneurysm via the lumen while the chemical crosslinking is ongoing; and
   delivering the biopolymer and the chemical crosslinking agent from the lumen into the internal volume via the exit port while the chemical crosslinking is ongoing.

2. The method of Clause 1 wherein the aneurysm is an intracranial aneurysm.

3. The method of Clause 1 wherein:
   the biopolymer has a non-zero degree of chemical crosslinking before being mixed with the chemical crosslinking agent; and
   mixing the biopolymer and the chemical crosslinking agent includes mixing the biopolymer and the chemical crosslinking agent to increase the degree of chemical crosslinking.

4. The method of Clause 1 wherein delivering the biopolymer and the chemical crosslinking agent from the lumen into the internal volume includes delivering the biopolymer and the chemical crosslinking agent from the lumen into the internal volume as components of a single cohesive strand that at least partially agglomerates to form a mass occupying at least 75% of the internal volume, and wherein the internal volume is a total internal volume of the aneurysm.

5. The method of Clause 1, further comprising:
   flowing a physical crosslinking agent toward the internal volume via the lumen with the biopolymer and the chemical crosslinking agent; and
   delivering the physical crosslinking agent from the lumen into the internal volume via the exit port with the biopolymer and the chemical crosslinking agent.

6. The method of Clause 5 wherein:
   the biopolymer includes chitosan, a derivative of chitosan, an analog of chitosan, or a combination thereof;
   the chemical crosslinking agent includes genipin, a derivative of genipin, an analog of genipin, or a combination thereof; and
   the physical crosslinking agent includes β-glycerophosphate, a derivative of β-glycerophosphate, an analog of β-glycerophosphate, or a combination thereof.

7. The method of Clause 1 wherein the biopolymer includes chitosan, a derivative of chitosan, an analog of chitosan, or a combination thereof.

8. The method of Clause 7 wherein the chemical crosslinking agent includes genipin, a derivative of genipin, an analog of genipin, or a combination thereof.

9. The method of Clause 8 wherein mixing the biopolymer and the chemical crosslinking agent includes mixing the biopolymer and the chemical crosslinking agent such that a weight ratio of the biopolymer to the chemical crosslinking agent is within a range from 10:1 to 100:1.

10. The method of Clause 1, further comprising reinforcing a neck of the aneurysm while the biopolymer and the chemical crosslinking agent are disposed within the internal volume and while the chemical crosslinking is ongoing.

11. The method of Clause 10, further comprising:
intravascularly advancing a balloon toward the portion of the blood vessel while the balloon is in a low-profile state; and
moving the balloon from the low-profile state toward an expanded state after advancing the balloon toward the portion of the blood vessel,
wherein reinforcing the neck includes reinforcing the neck with the balloon in the expanded state.

12. The method of Clause 10, further comprising:
intravascularly advancing a tubular flow diverter toward the portion of the blood vessel while the flow diverter is in a low-profile state; and
moving the flow diverter from the low-profile state toward an expanded state after advancing the flow diverter toward the portion of the blood vessel,
wherein reinforcing the neck includes reinforcing the neck with the flow diverter in the expanded state.

13. A method for treating an aneurysm, the method comprising:
disposing a tissue scaffold material including biopolymer and a chemical crosslinking agent within an internal volume of an aneurysm at a portion of a blood vessel, wherein the tissue scaffold material has a first storage modulus on a pascal scale immediately after being disposed within the internal volume;
reinforcing a neck of the aneurysm while the tissue scaffold material is disposed within the internal volume and while chemical crosslinking of the biopolymer is occurring; and
reducing reinforcement of the neck, wherein the tissue scaffold material has a second storage modulus on a pascal scale immediately after reducing reinforcement of the neck, and wherein the second storage modulus is at least 20% greater than the first storage modulus.

14. The method of Clause 13 wherein the aneurysm is an intracranial aneurysm.

15. The method of Clause 13 wherein:
the chemical crosslinking has an endpoint at which the tissue scaffold material has a third storage modulus on a pascal scale; and
the first storage modulus is within a range from 40% to 80% of the third storage modulus.

16. The method of Clause 13 wherein disposing the tissue scaffold material within the internal volume includes delivering the tissue scaffold material into the internal volume as a single cohesive strand that at least partially agglomerates to form a mass occupying at least 75% of the internal volume, and wherein the internal volume is a total internal volume of the aneurysm.

17. The method of Clause 13 wherein the tissue scaffold material includes a physical crosslinking agent.

18. The method of Clause 17 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes $\beta$-glycerophosphate, a derivative of $\beta$-glycerophosphate, an analog of $\beta$-glycerophosphate, or a combination thereof.

19. The method of Clause 13 wherein the biopolymer includes chitosan, an analog of chitosan, or a combination thereof.

20. The method of Clause 19 wherein the chemical crosslinking agent includes genipin, a derivative of genipin, an analog of genipin, or a combination thereof.

21. The method of Clause 20 wherein a weight ratio of the biopolymer to the chemical crosslinking agent within the tissue scaffold material is within a range from 10:1 to 100:1.

22. A system for treating an aneurysm, the system comprising:
a first precursor material including a biopolymer;
a second precursor material including a chemical crosslinking agent; and
a catheter including an elongate lumen and an exit port at a distal end portion of the lumen, wherein the catheter is configured to convey a mixture of the first and second precursor materials toward and into an internal volume of an aneurysm at a portion of a blood vessel via the lumen and via the exit port, and wherein the catheter is at most 3 French.

23. The system of Clause 22, wherein the biopolymer has a non-zero degree of chemical crosslinking within the first precursor material.

24. The system of Clause 22 wherein:
(a) the first precursor material includes a physical crosslinking agent;
(b) the second precursor material includes a physical crosslinking agent;
(c) the system further comprises a third precursor material including a physical crosslinking agent; or
(d) any combination of (a), (b) and (c).

25. The system of Clause 24 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes $\beta$-glycerophosphate, a derivative of $\beta$-glycerophosphate, an analog of $\beta$-glycerophosphate, or a combination thereof.

26. The system of Clause 22 wherein the biopolymer includes chitosan, a derivative of chitosan, an analog of chitosan, or a combination thereof.

27. The system of Clause 26 wherein the chemical crosslinking agent includes genipin, a derivative of genipin, an analog of genipin, or a combination thereof.

28. The system of Clause 22 wherein:
(a) the first precursor material includes a contrast agent;
(b) the second precursor material includes a contrast agent;
(c) the system further comprises a third precursor material including a contrast agent; or
(d) any combination of (a), (b) and (c).

29. The system of Clause 28 wherein the contrast agent is selected to provide diminishing radiopacity.

30. The system of Clause 28 wherein the contrast agent includes iohexol, a derivative of iohexol, an analog of iohexol, or a combination thereof.
31. A method for at least partially filling a volume at a treatment location, the method comprising:
advancing a catheter toward the treatment location, wherein the catheter includes an elongate lumen and an exit port at a distal end portion of the lumen;
mixing a biopolymer and a chemical crosslinking agent to initiate chemical crosslinking of the biopolymer;
flowing the biopolymer and the chemical crosslinking agent toward the volume via the lumen while the chemical crosslinking is ongoing; and
delivering the biopolymer and the chemical crosslinking agent from the lumen into the volume via the exit port while the chemical crosslinking is ongoing.
32. The method of Clause 31, wherein advancing the catheter comprises advancing the catheter through a blood vessel.
33. The method of Clause 31, wherein the treatment location comprises an aneurysm and the volume comprises an internal volume of the aneurysm.
34. The method of Clause 31, wherein the treatment location comprises a vein and the volume comprises a lumen of the vein.
35. The method of Clause 34, wherein the vein is located in a leg.
36. The method of Clause 35, further comprising reducing leg vein varicosity by occluding the vein lumen via said delivering.
37. The method of Clause 31, wherein the treatment location comprises an artery that vascularizes a tumor and the volume comprises a lumen of the artery.
38. The method of Clause 31, wherein the treatment location comprises a vascular or cardiovascular implant and the volume comprises an endoleak.
39. The method of Clause 31 wherein:
the biopolymer has a non-zero degree of chemical crosslinking before being mixed with the chemical crosslinking agent; and
mixing the biopolymer and the chemical crosslinking agent includes mixing the biopolymer and the chemical crosslinking agent to increase the degree of chemical crosslinking.
40. The method of Clause 31 wherein delivering the biopolymer and the chemical crosslinking agent from the lumen into the volume includes delivering the biopolymer and the chemical crosslinking agent from the lumen into the volume as components of a single cohesive strand that at least partially agglomerates to form a mass occupying at least 75% of the volume, and wherein the volume is a total internal volume of an aneurysm.
41. The method of Clause 31, further comprising:
flowing a physical crosslinking agent toward the volume via the lumen with the biopolymer and the chemical crosslinking agent; and
delivering the physical crosslinking agent from the lumen into the volume via the exit port with the biopolymer and the chemical crosslinking agent.
42. The method of Clause 41 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β-glycerophosphate, a derivative of β-glycerophosphate, an analog of β-glycerophosphate, or a combination thereof.
43. The method of Clause 31 wherein the biopolymer includes chitosan, a derivative of chitosan, an analog of chitosan, or a combination thereof.
44. The method of Clause 43 wherein the chemical crosslinking agent includes genipin, a derivative of genipin, an analog of genipin, or a combination thereof.
45. The method of Clause 44 wherein mixing the biopolymer and the chemical crosslinking agent includes mixing the biopolymer and the chemical crosslinking agent such that a weight ratio of the biopolymer to the chemical crosslinking agent is within a range from 10:1 to 100:1.
46. The method of Clause 31, wherein the treatment location comprises an aneurysm and the volume comprises an internal volume of the aneurysm, and further comprising reinforcing a neck of the aneurysm while the biopolymer and the chemical crosslinking agent are disposed within the internal volume and while the chemical crosslinking is ongoing.
47. The method of Clause 46, further comprising:
intravascularly advancing a balloon toward a portion of a blood vessel near the aneurysm while the balloon is in a low-profile state; and
moving the balloon from the low-profile state toward an expanded state after advancing the balloon toward the portion of the blood vessel,
wherein reinforcing the neck includes reinforcing the neck with the balloon in the expanded state.
48. The method of Clause 47, further comprising:
intravascularly advancing a tubular flow diverter toward the portion of the blood vessel while the flow diverter is in a low-profile state; and
moving the flow diverter from the low-profile state toward an expanded state after advancing the flow diverter toward the portion of the blood vessel,
wherein reinforcing the neck includes reinforcing the neck with the flow diverter in the expanded state.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical, similar, or analogous components or features of more than one embodiment of the present technology.

DETAILED DESCRIPTION

Figure 1:
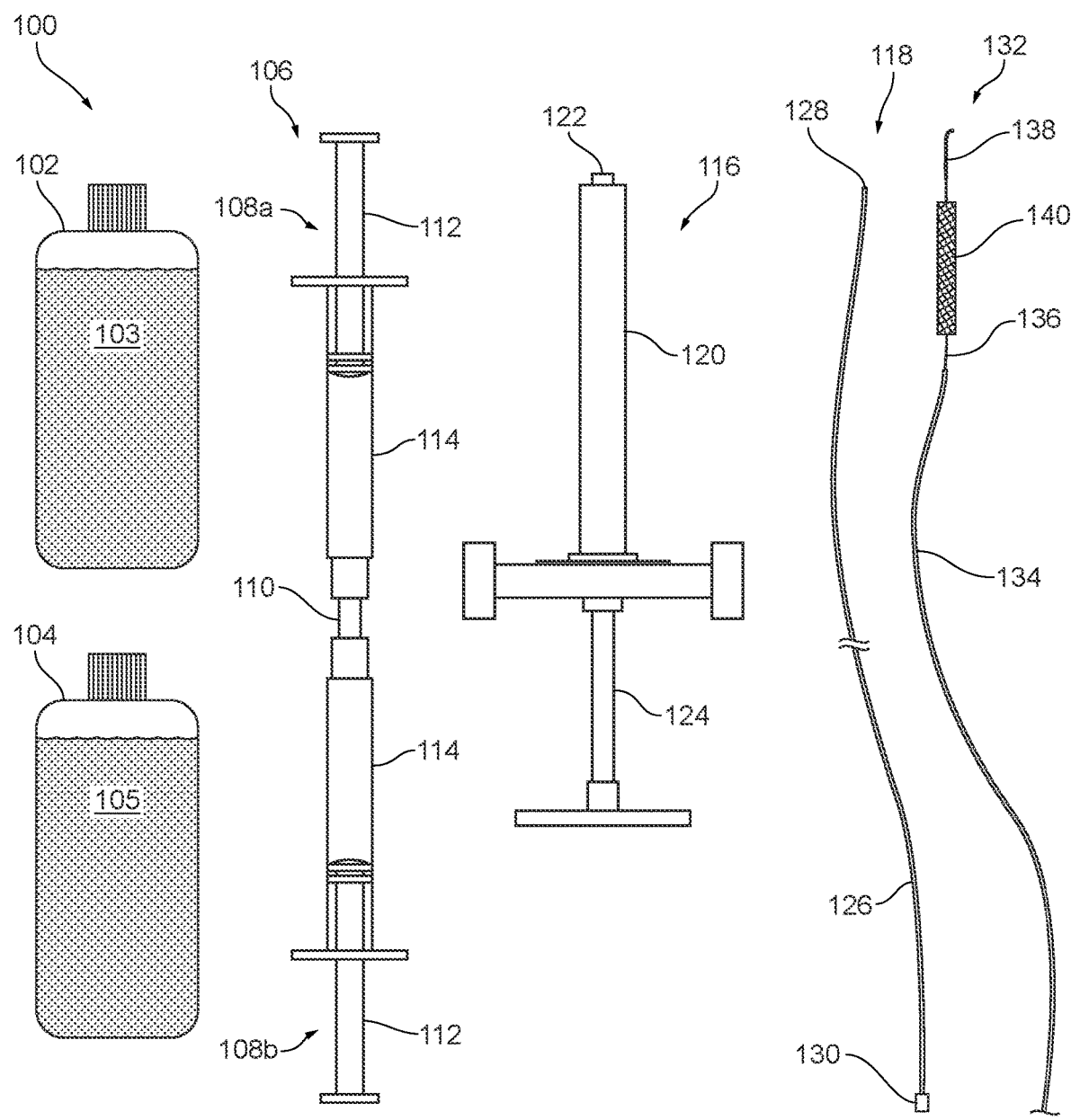
FIG. 1 is a top plan view of a system for treating intracranial aneurysms in accordance with an embodiment of the present technology.

Systems, devices, and methods in accordance with embodiments of the present technology can at least partially address one or more problems associated with conventional technologies whether or not such problems are stated herein. Methods for treating intracranial aneurysms in accordance with at least some embodiments of the present technology include introducing an injectable scaffold material into the internal volume of an intracranial aneurysm (aneurysm internal volume). In animal studies, such methods have been found to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

Specific details of systems, devices, and methods for treating intracranial aneurysms in accordance with embodiments of the present technology are described herein with reference to FIGS. 1-15. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

FIG. 1 is a top plan view of a system 100 for treating intracranial aneurysms in accordance with an embodiment of the present technology. The system 100 can include a first container 102 containing a first precursor material 103 (shown schematically), a second container 104 containing a second precursor material 105 (also shown schematically), and a mixing device 106 suitable for mixing the first and second precursor materials 103, 105. The mixing device 106 can include mixing syringes 108 (individually identified as mixing syringes 108a, 108b) and a coupler 110 extending between respective exit ports (not shown) of the mixing syringes 108. The mixing syringes 108a, 108b each include a plunger 112 and a barrel 114 in which the plunger 112 is slidably received.

The system 100 can further include an injection syringe 116 and a first catheter 118 configured to deliver and receive, respectively, a mixture of the first and second precursor materials 103, 105 from the injection syringe 116. The injection syringe 116 can include a barrel 120, an exit port 122 at one end of the barrel 120, and a plunger 124 slidably received within the barrel 120 via an opposite end of the barrel 120. The first catheter 118 can include an elongate shaft 126 defining an elongate lumen (not shown), an exit port 128 at a distal end portion of the lumen, and a coupler 130 at a proximal end portion of the lumen. The coupler 130 can be configured to form a secure fluidic connection between the lumen and the exit port 122 of the injection syringe 116. The first catheter 118 can be configured to receive a mixture of the first and second precursor materials 103, 105 from the injection syringe 116 via the coupler 130 and to convey the mixture toward and into the internal volume of an intracranial aneurysm (or other treatment location such as any of those described herein) via the lumen and via the exit port 128. The system 100 can further include a second catheter 132 including an elongate sheath 134 and a wire 136 slidably disposed within the sheath 134. At a distal end portion of the wire 136, the second catheter 132 can include an atraumatic hook 138. The first and second catheters 118, 132 can be steerable or non-steerable and can be configured for deployment by guide wire, by guide sheath, or in another suitable manner. Furthermore, the first and second catheters 118, 132 can be of suitable sizes to both be located within an intracranial blood vessel at the same time. In at least some cases, the first catheter 118 is at most 3 French and/or the second catheter 132 is at most 3 French.

The system 100 can also include a tubular stent such as a flow diverter 140 carried by the second catheter 132 proximal to the hook 138. The flow diverter 140 can have an expanded state (as shown) and a low-profile state (e.g., a collapsed state) in which the flow diverter 140 is sufficiently compact to move longitudinally within the sheath 134. In at least some cases, the flow diverter 140 includes filaments that shift relative to one another as the flow diverter 140 moves between its expanded and low-profile states. The flow diverter 140, for example, can be a braided tube.

Figure 2:
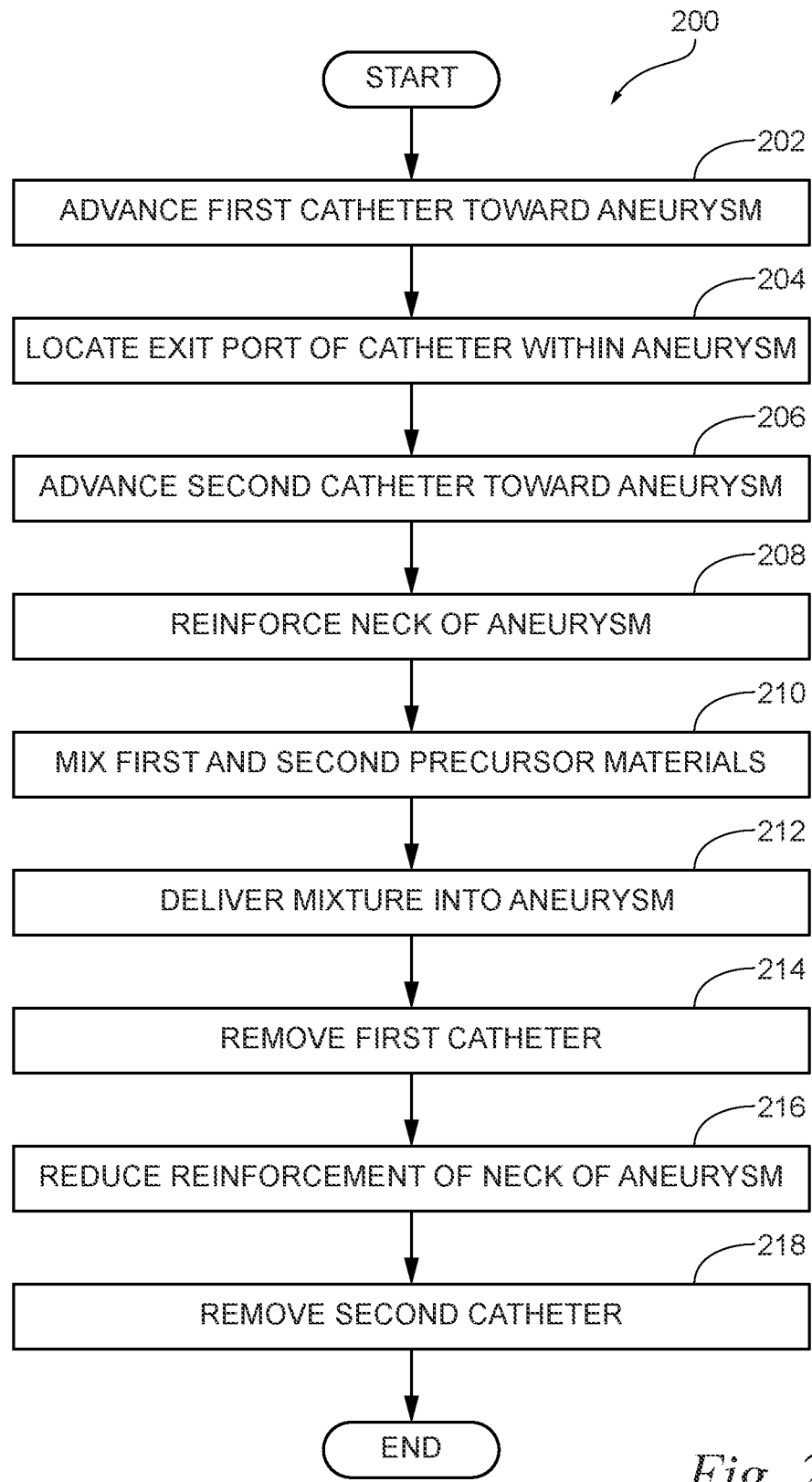
FIG. 2 is a flow chart illustrating a method for treating an intracranial aneurysm in accordance with an embodiment of the present technology.
Figure 3:
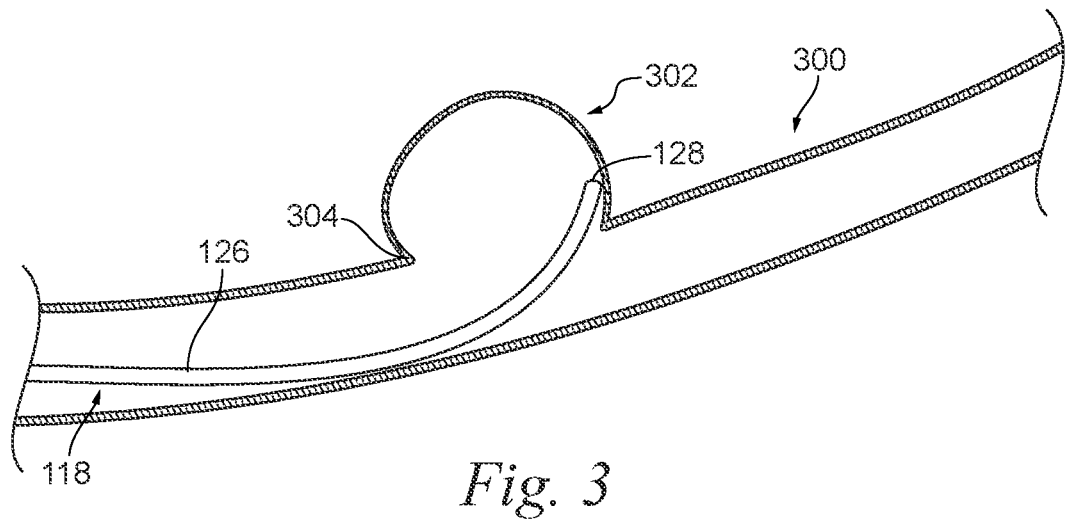
FIGS. 3-12 are anatomical side views of portions of the system shown in FIG. 1 within an intracranial blood vessel at different respective stages during the method shown in FIG. 2.

FIG. 2 is a flow chart illustrating a method 200 for treating an intracranial aneurysm in accordance with an embodiment of the present technology, and FIGS. 3-12 are anatomical side views of portions of the system 100 within an intracranial blood vessel 300 at different respective stages during the method 200. With reference first to FIGS. 2 and 3 together, the method 200 can include intravascularly advancing the first catheter 118 toward an intracranial aneurysm 302 (or other treatment location such as any of those described herein) along the blood vessel 300 (block 202). The method 200 can further include extending the shaft 126 though a neck 304 of the aneurysm 302 to locate the exit port 128 within an internal volume of the aneurysm 302 (block 204). Portions of the first catheter 118 around the exit port 128 can be atraumatic to avoid damaging the aneurysm 302 during positioning of the exit port 128. Although the internal volume of the aneurysm 302 is empty of non-anatomical material or structures in the illustrated embodiment, in other embodiments, the internal volume of the aneurysm 302 may contain such material or structures. For example, the internal volume of the aneurysm 302 may contain a previously introduced embolization coil or mesh. Therefore, the various embodiments of the method 200 can further comprise introduction of a permanent intrasaccular device such as an embolization coil or mesh embolization device (e.g. a mesh coil having a series of expanding petals such as the MEDINA™ Embolization Device from Medtronic). Such embodiments of the method can comprise introducing one or more such permanent intrasaccular devices into the aneurysm before delivering the scaffold material into the aneurysm.

Figure 4:
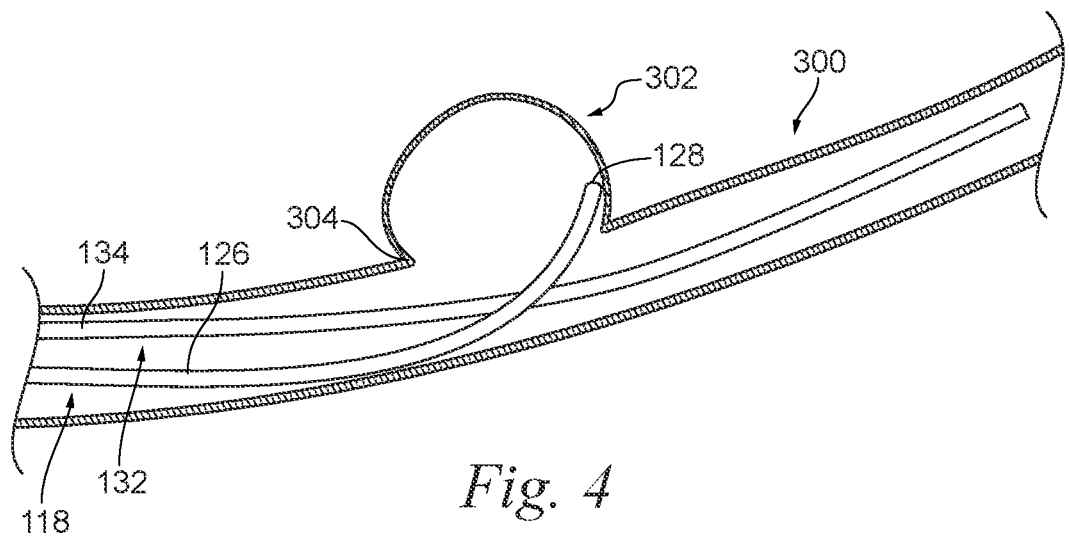
Figure 5:
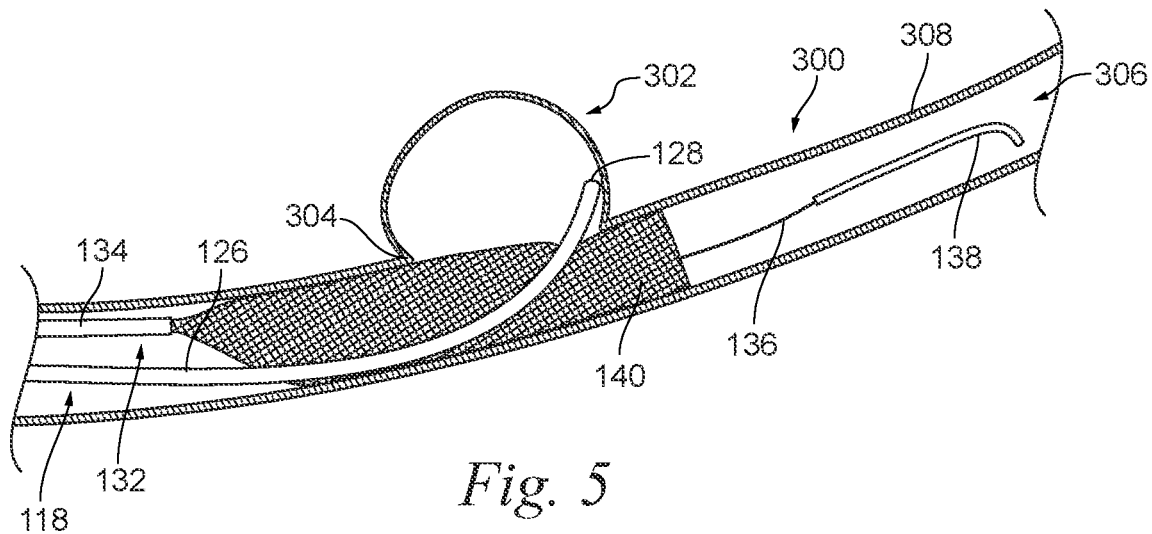

With reference now to FIGS. 1, 2 and 4 together, the method 200 can further include advancing the second catheter 132 toward the aneurysm 302 (block 206) while the flow diverter 140 (FIG. 1) is in its low-profile state. Next, with reference to FIGS. 1, 2 and 5 together, the method 200 can include reinforcing the neck 304 (block 208) by moving the flow diverter 140 from its low-profile state toward its expanded state within a main lumen 306 of the blood vessel 300. In addition to reinforcing the neck 304, the flow diverter 140 can stabilize the position of the exit port 128 within the aneurysm 302 by pressing a portion of the shaft 126 against a wall 308 of the blood vessel 300. In an alternative embodiment, the flow diverter 140 is replaced with a balloon configured to be intravascularly advanced in a low-profile state (e.g., a deflated state) and deployed in an expanded state (e.g., an at least partially inflated state). Use of a balloon in place of a flow diverter may be advantageous, for example, when the intravascular anatomy around an aneurysm is not suitable for deploying a flow diverter. In some cases, a balloon that replaces the flow diverter 140 is a tubular balloon having an annular form or another suitable form with a longitudinal flow passage therethrough for avoiding complete or near complete occlusion of a blood vessel in which the balloon is deployed. Alternatively, a balloon that lacks such a flow passage may be used when such complete or near complete occlusion of a blood vessel is acceptable.

Figure 6:
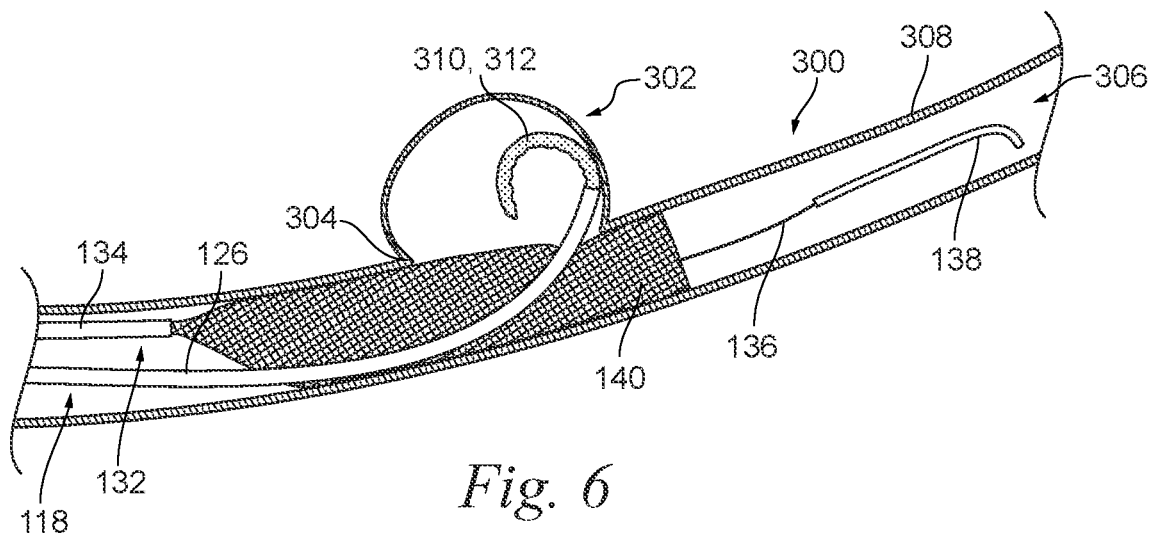

With reference to FIGS. 1, 2 and 6 together, the method 200 can include mixing the first and second precursor materials 103, 105 (block 210) to form a tissue scaffold material 310. In a particular example, the first precursor material 103 is loaded into one of the barrels 114, the second precursor materials 105 is loaded into the other barrel 114, and the mixing syringes 108 are coupled via the coupler 110. To mix the first and second precursor materials 103, 105, the plungers 112 are alternately depressed, thereby causing the first and second precursor materials 103, 105 to move repeatedly from one barrel 114 to the other barrel 114. After suitably mixing the precursor materials, the resulting tissue scaffold material 310 can be loaded into the barrel 120 of the injection syringe 116. When the lumen within the first catheter 118 is very narrow (e.g., when the first catheter 118 is at most 3 French), a considerable amount of pressure may be necessary to move the tissue scaffold material 310 through the lumen to the aneurysm 302. Accordingly, the injection syringe 116 is configured to withstand high pressure, such as at least 500 psi.

The first and second precursor materials 103, 105 (FIG. 1) can include a biopolymer and a chemical crosslinking agent, respectively. The chemical crosslinking agent can be selected to form covalent crosslinks between chains of the biopolymer. In some embodiments, the biopolymer of the first precursor material 103 includes chitosan or a derivative or analog thereof, and the chemical crosslinking agent of the second precursor material 105 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 103 can include collagen or a derivative or analog thereof, and the chemical crosslinking agent of the second precursor material 105 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 103 and the chemical crosslinking agent of the second precursor material 105 can include other suitable compounds alone or in combination.

Mixing the biopolymer of the first precursor material 103 and the chemical crosslinking agent of the second precursor material 105 can initiate chemical crosslinking of the biopolymer. After the first and second precursor materials 103, 105 are mixed, chemical crosslinking of the biopolymer occurs for enough time to allow the resulting tissue scaffold material 310 to be delivered to the aneurysm 302 before becoming too viscous to move through the lumen of the first catheter 118. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the tissue scaffold material 310 to remain within the internal volume of the aneurysm 302 without reinforcing the neck 304.

In at least some cases, the biopolymer has a non-zero degree of chemical crosslinking within the first precursor material 103 before mixing with the chemical crosslinking agent. This can be useful, for example, to customize the curing window for the tissue scaffold material 310 so that it corresponds well with an expected amount of time needed to deliver the material to the aneurysm 302. The degree of chemical crosslinking of the biopolymer within the first precursor material 103 before mixing with the chemical crosslinking agent, the ratio of the biopolymer to the chemical crosslinking agent, and/or one or more other variables can be selected to cause the tissue scaffold material 310 to have a viscosity suitable for delivery to the aneurysm 302 via the lumen of the first catheter 118 for a suitable period of time (e.g., a period within a range from 10 minutes to 40 minutes) after mixing of the first and second precursor materials 103, 105. In at least some cases, the first and second precursor materials 103, 105 are mixed in proportions that cause a weight ratio of the biopolymer to the chemical crosslinking agent in the resulting tissue scaffold material 310 to be within a range from 10:1 to 100:1, such as from 10:1 to 30:1, or from 15:1 to 50:1, or from 15:1 to 25:1. In a particular example, the first and second precursor materials 103, 105 are mixed in proportions that cause a weight ratio of the biopolymer to the chemical crosslinking agent in the resulting tissue scaffold material 310 to be 30:1.

Use of a biopolymer instead of an artificial polymer in the first precursor material 103 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 105 may be advantageous because chemically crosslinked polymers tend to be more cohesive than physically crosslinked polymers and/or for other reasons. In the context of forming a tissue scaffold within an aneurysm, high cohesiveness of the tissue scaffold material 310 may be more important than it is in other contexts to secure the cured tissue scaffold material 310 within the aneurysm 302. For example, high cohesiveness of the tissue scaffold material 310 may reduce or eliminate the possibility of a piece of the tissue scaffold material 310 breaking free and entering a patient's intracerebral blood stream during delivery.

The first and second precursor materials 103, 105 may include other components and/or the system 100 may include other precursor materials intended for mixing with the first and second precursor materials 103, 105. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the tissue scaffold material 310. Suitable physical crosslinking agents for use with chitosan-based biopolymers include R glycerophosphate, mannitol, glucose, and derivatives and analogs thereof. In these and other cases, the tissue scaffold material 310 may include multiple chemical crosslinking agents and/or multiple physical crosslinking agents.

A contrast agent is another component that may be added to the precursor materials. The presence of a contrast agent within the tissue scaffold material 310 can be useful to visualize delivery of the tissue scaffold material 310 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the tissue scaffold material 310 is selected to provide radiopacity that diminishes over time. For example, the contrast agent may initially be radiopaque to facilitate delivery of the tissue scaffold material 310 and then become less radiopaque to facilitate follow-up imaging. In a particular example, the first, second, and/or another precursor material includes iohexol or a derivative or analog thereof as a suitable contrast agent.

Figure 7:
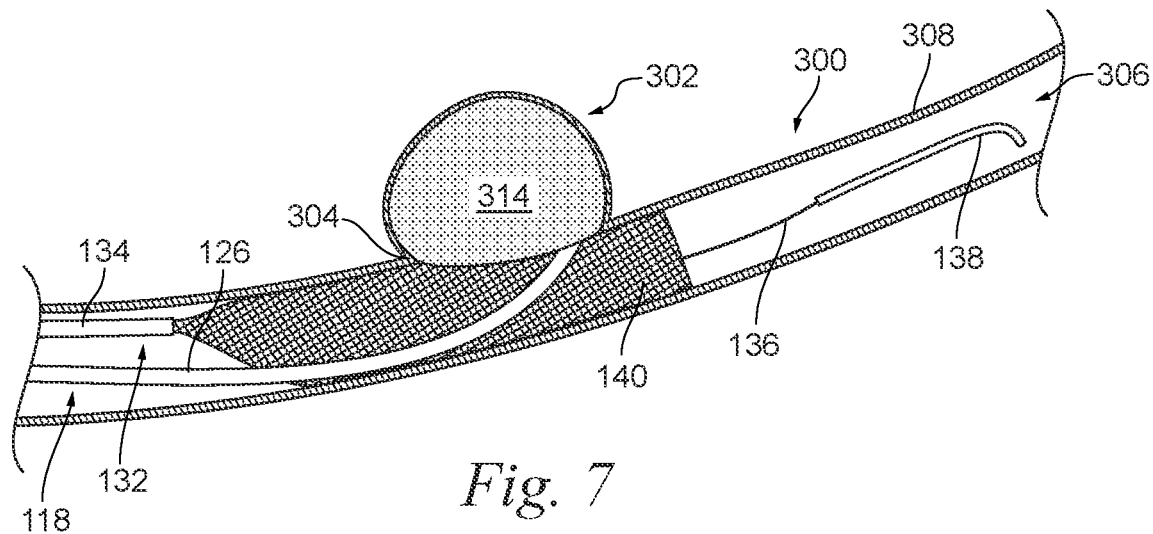

With reference again to FIGS. 1, 2 and 6 together, the method 200 can include delivering the tissue scaffold material 310 into an internal volume of the aneurysm 302 (block 212). For example, the method 200 can include delivering the tissue scaffold material 310 through the lumen of the first catheter 118 so that the tissue scaffold material 310 flows through the exit port 128 of the first catheter 118 and into the aneurysm 302. As the tissue scaffold material 310 passes through the lumen of the first catheter 118, chemical crosslinking of the biopolymer can continue to occur. As shown in FIG. 6, the tissue scaffold material 310 can exit the exit port 128 of the first catheter 118 as a single cohesive strand 312. As shown in FIG. 7, as more tissue scaffold material 310 is delivered to the aneurysm 302, the strand 312 can at least partially agglomerate to form a mass 314. In the illustrated embodiment, the mass 314 occupies all of the internal volume of the aneurysm 302 and the area of the aneurysm neck 304. In other embodiments, the mass 314 can occupy less than all (e.g., from 20% to 100%, from 50% to 100%, or from 75% to 100%) of the total internal volume of the aneurysm 302, particularly but not exclusively when used in combination with additional aneurysm treatments such as embolic coils or implants.

Figure 8:
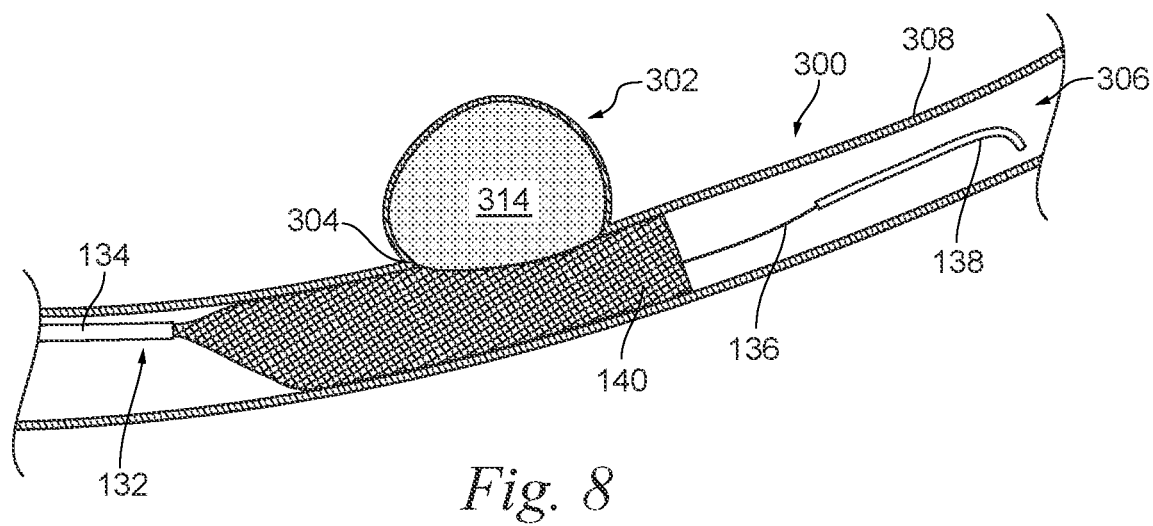

With reference to FIGS. 1, 2 and 8, the method 200 can include removing the first catheter 118 (block 214) after forming the mass 314. The method 200 can further include reinforcing the neck 304 while the tissue scaffold material 310 is disposed within the internal volume of the aneurysm 302 and while chemical crosslinking of the biopolymer continues to occur. The neck 304 can be obstructed by the combination of the mass 314 and the flow diverter 140 (or balloon or other luminal intraluminal device(s)) holding the mass 314 in place until sufficient chemical crosslinking of the biopolymer has occurred.

Figure 9:
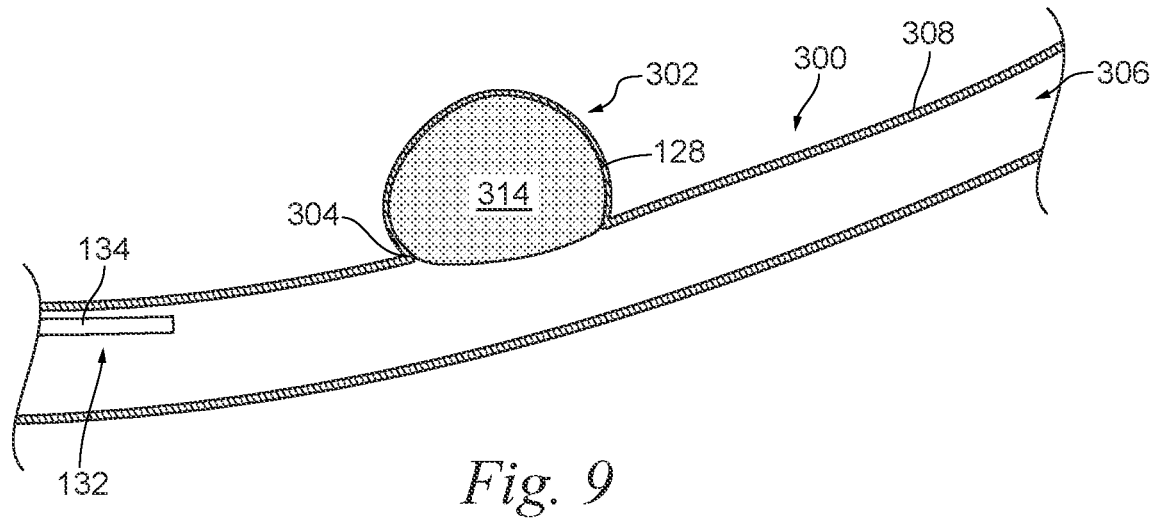

With reference to FIGS. 1, 2 and 9, the method 200 can also include reducing or removing reinforcement of the neck 304 (block 216). For example, the flow diverter 140 can be moved from its expanded state toward its low-profile state and simultaneously or subsequently retracted into the sheath 134. After the tissue scaffold material 310 is disposed within the internal volume of the aneurysm 302 and before the reinforcement of the neck 304 is reduced or removed, the number of chemical crosslinks within the tissue scaffold material 310 may increase by at least 5%, at least 10%, or at least 15%. In at least some cases, the tissue scaffold material 310 has a first storage modulus on a pascal scale immediately after being disposed within the internal volume of the aneurysm 302, a second storage modulus on a pascal scale immediately after reinforcement of the neck 304 is reduced, and a third storage modulus on a pascal scale at an endpoint of the chemical crosslinking. The second storage modulus can be at least 20% greater than the first storage modulus. Furthermore, the first storage modulus can be within a range from 40% to 80% of the third storage modulus.

Figure 10:
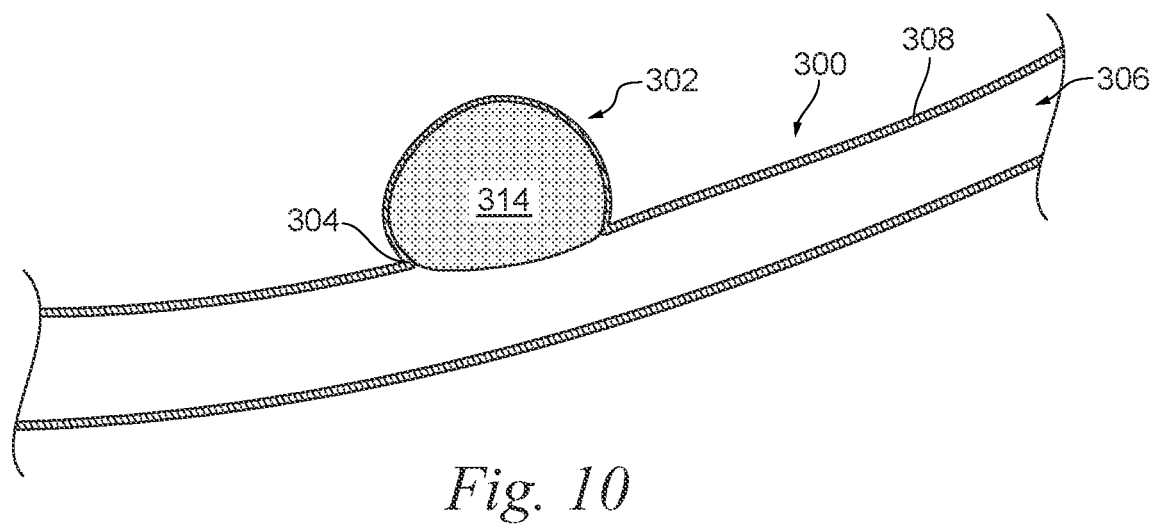
Figure 11:
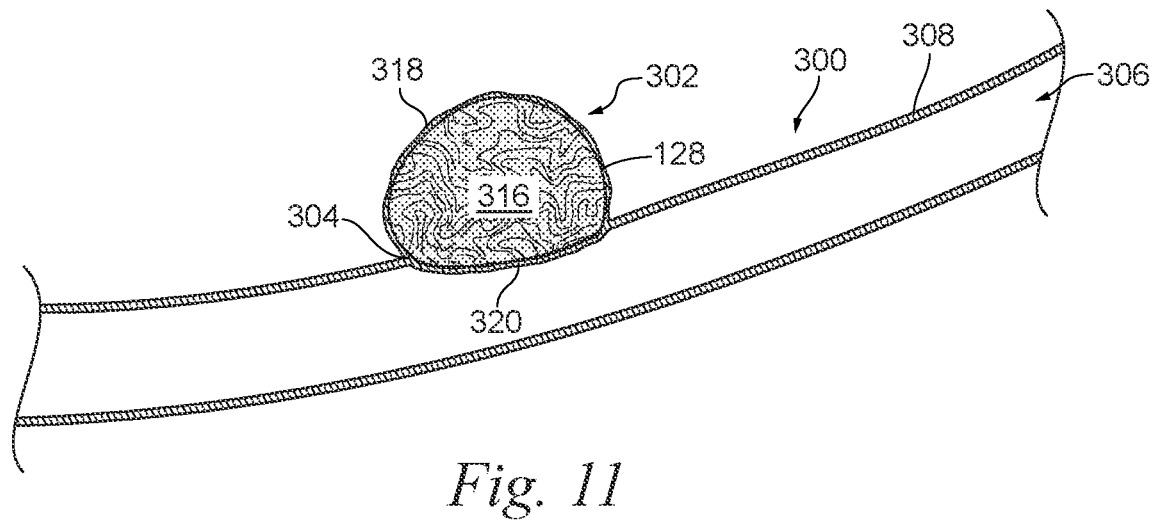
Figure 12:
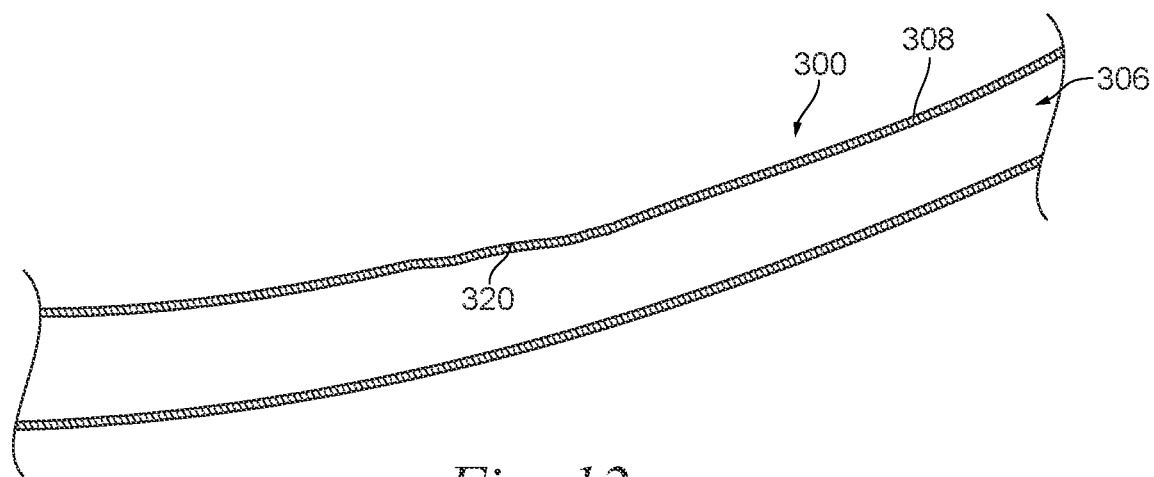

After the flow diverter 140 has been stowed within the sheath 134, the method 200 can include removing the second catheter 132 (block 218). As shown in FIG. 10, the mass 314 can remain securely lodged within the internal volume of the aneurysm 302 after the second catheter 132 is removed. Over time, as shown in FIG. 11, natural vascular remodeling mechanisms and/or bioabsorption of the mass 314 may lead to formation of a thrombus 316 and/or conversion of entrapped thrombus 316 to fibrous tissue within the internal volume of the aneurysm 302. These mechanisms also may lead to cell death at a wall 318 of the aneurysm 302 and growth of new endothelial cells 320 along a surface of the thrombus 316 bordering the main lumen 306 of the blood vessel 300. Eventually, the thrombus 316 and the cells at the wall 318 of the aneurysm 302 may fully degrade, leaving behind a successfully remodeled region of the blood vessel 300 (FIG. 12). In should be noted that, although the flow diverter 140 is removed in the illustrated embodiment, in other embodiment, the flow diverter 140 can be left in place. In these embodiments, the new endothelial cells 320 can grow between and over filaments or struts of the flow diverter 140.

EXAMPLES

The following examples are provided to illustrate certain particular embodiments of the disclosure. It should be understood that additional embodiments not limited to the particular features described are consistent with the following examples.

Example 1—Tissue Scaffold Material

Figure 13:
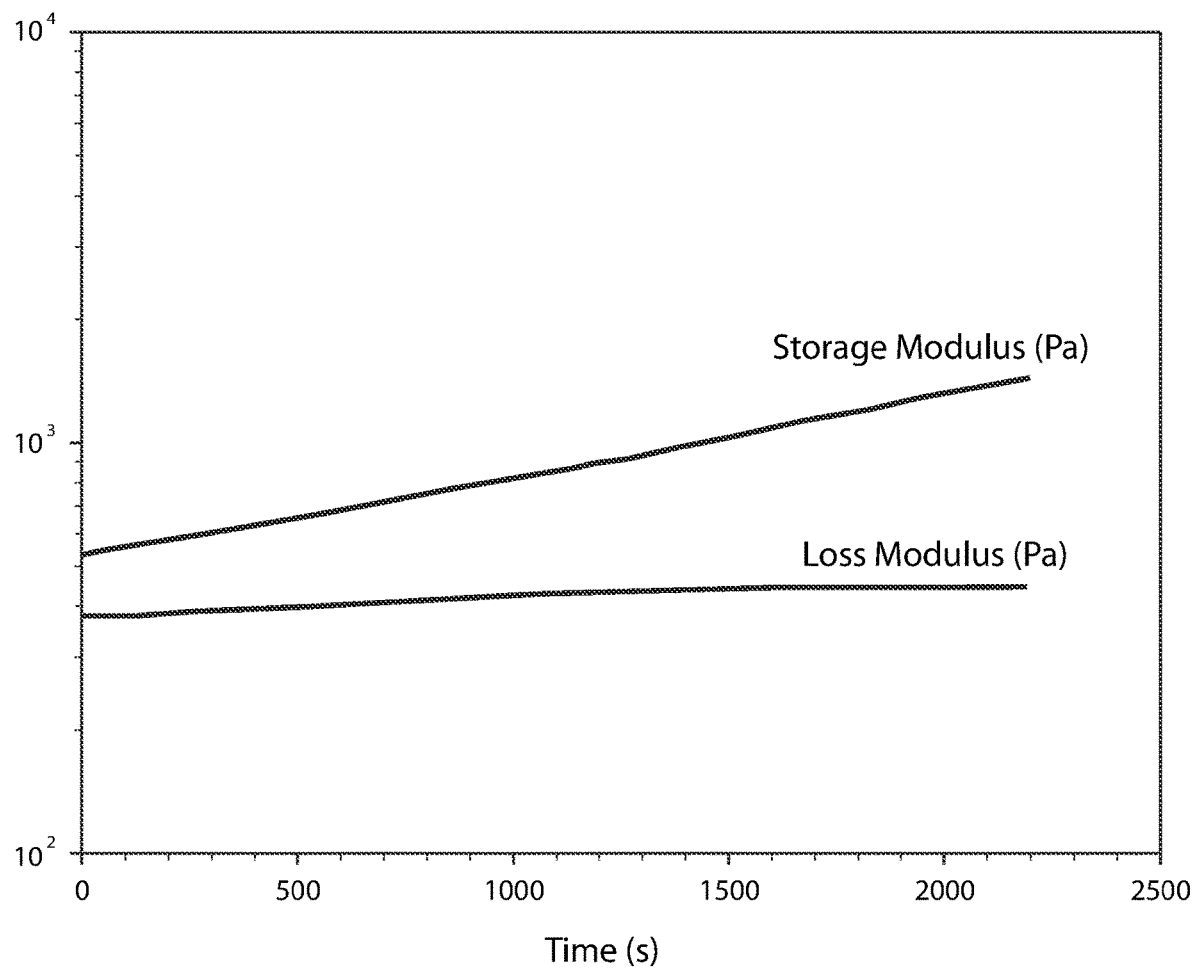
FIG. 13 is a plot of storage modulus (measured by rheometer) and loss modulus (also measured by rheometer) relative to time for a tissue scaffold material in accordance with an embodiment of the present technology.
Figure 14:
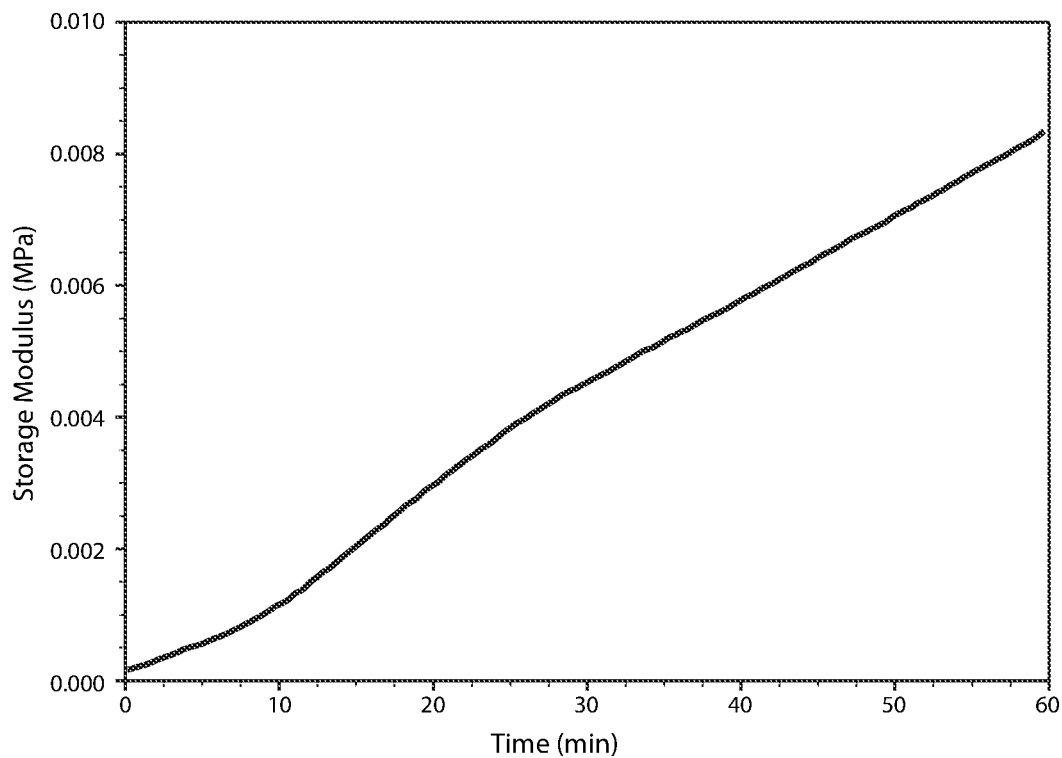
FIGS. 14 and 15 are plots, respectively, of storage modulus (measured by dynamic mechanical analysis) and loss modulus (also measured by dynamic mechanical analysis) relative to time for the tissue scaffold material of FIG. 13.
Figure 15:
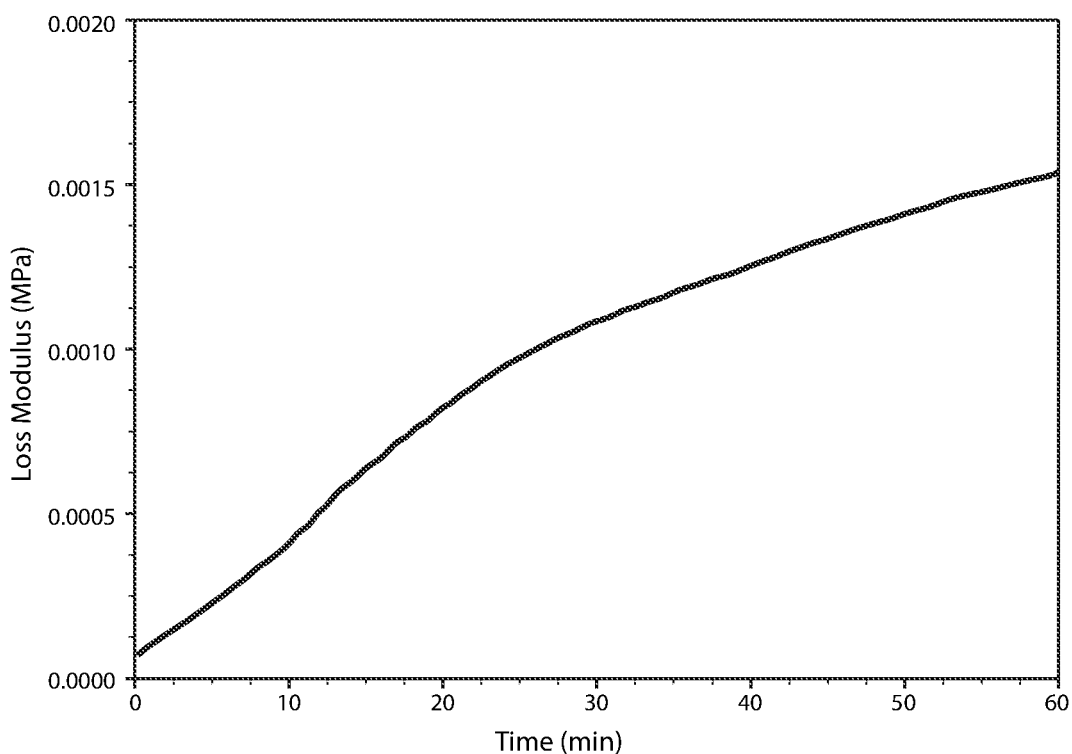

A tissue scaffold material was prepared as a solution of 3.8% chitosan, 2.9% R glycerophosphate, and 0.1% genipin (all percentages weight/volume). The ratio of genipin to chitosan in the resulting tissue scaffold material was 38:1. FIG. 13 is a plot of storage modulus and loss modulus relative to time for the tissue scaffold material. The values in FIG. 13 were measured by rheometer beginning 2 minutes after mixing the solutions. Similarly, FIGS. 14 and 15 are plots, respectively, of storage modulus and loss modulus relative to time for the tissue scaffold material. The values in FIGS. 14 and 15 were measured by dynamic mechanical analysis beginning 30 minutes after mixing the solutions. Tissue scaffold materials in accordance with some embodiments of the present technology have storage modulus and/or loss modulus values at a given time after mixing within 25% (e.g., within 10%) of the corresponding values shown in FIGS. 13-15. Tissue scaffold materials in accordance with other embodiments of the present technology can have other suitable storage modulus and loss modulus values.

Example 2—Bench Test

A flow loop with a model aneurysm (10 mm pouch diameter; 4 mm neck diameter) was used for bench testing the tissue scaffold material (Example 1). The distal end of a MARKSMAN® (ID 0.027") microcatheter was located within the model aneurysm and secured by deploying a PIPELINE FLEX™ Embolization Device (Medtronic) ("P-Flex device") across the neck of the model aneurysm. The tissue scaffold material was injected into the model aneurysm via the microcatheter within 10 minutes of mixing the chitosan, R glycerophosphate, and genipin solutions. The resulting mass of tissue scaffold material was found to be stable within the model aneurysm for 2 hours under simulated pulsatile blood flow of 600 mL per minute.

Example 3—Animal Test (9-Day Follow Up)

Two model aneurysms (distal and proximal) were created in the carotid artery of each of two canine subjects. The model aneurysms had pouch diameters of approximately 10 mm and neck diameters of approximately 4 mm. Tissue scaffold material (Example 1) was injected into the distal and proximal model aneurysms of the first subject and into the distal model aneurysm of the second subject via the microcatheter (Example 2). P-Flex devices were deployed across the neck of the proximal model aneurysm of the first subject and across the necks of the distal and proximal model aneurysms of the second subject. After 9 days, the subject animals were euthanized and the model aneurysms were biopsied. The biopsies showed that the model aneurysms having the tissue scaffold material and a P-Flex device contained well-developed aneurismal thrombi encompassing all or nearly all of the model aneurysms' internal volumes. The model aneurysm having the tissue scaffold material and not having a P-Flex device included an aneurismal thrombus encompassing most of the model aneurysm's internal volume, but with some vacant areas at the perimeter of the internal volume near the model aneurysm's neck. The model aneurysm having a P-Flex device and not having the tissue scaffold material did not contain an aneurismal thrombus. No inflammation was observed in the parent vessels.

Example 4—Animal Test (90-Day Follow Up)

Two model aneurysms (distal and proximal) were created in the carotid artery of each of two canine subjects. The model aneurysms had pouch diameters of approximately 10 mm and neck diameters of approximately 4 mm. Tissue scaffold material (Example 1) was injected into the distal model aneurysm of the first subject and into the distal and proximal model aneurysms of the second subject via the microcatheter (Example 2). Platinum coils were introduced into the proximal model aneurysm of the first subject. A P-Flex device and a SOLITAIRE® Stent were deployed, respectively, across the necks of the distal and proximal model aneurysms of the first subject. After 90 days, the subject animals were euthanized and the model aneurysms were biopsied. The biopsies showed that the model aneurysms having the tissue scaffold material and not having a P-Flex device or a SOLITAIRE® stent as well as the model aneurysm having the tissue scaffold material and the P-Flex device showed complete endothelial coverage at the aneurismal neck.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like may be used herein to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

We claim:

1. A system for treating an aneurysm, the system comprising:
a catheter comprising an elongate lumen and an exit port at a distal portion of the elongate lumen; and
a composition comprising a mixture of a biopolymer, a chemical crosslinking agent, and a physical crosslinking agent, wherein the mixture is configured to be delivered into an internal volume of the aneurysm via the elongate lumen and exit port of the catheter, and wherein the mixture is configured to be delivered as a cohesive strand and to at least partially agglomerate to form a mass within the internal volume.

2. The system of claim 1, wherein the biopolymer comprises chitosan or a derivative or an analog thereof.

3. The system of claim 1, wherein the chemical crosslinking agent comprises genipin or a derivative or an analog thereof.

4. The system of claim 1, wherein the physical crosslinking agent comprises β-glycerophosphate or a derivative or an analog thereof.

5. The system of claim 1, wherein the mixture further comprises a contrast agent.

6. The system of claim 5, wherein the contrast agent comprises iohexol or a derivative or an analog thereof.

7. The system of claim 1, further comprising a syringe configured to deliver the mixture into the elongate lumen of the catheter.

8. The system of claim 7, wherein the syringe is configured to withstand a pressure of at least 500 psi to move the mixture through the elongate lumen to the internal volume of the aneurysm.

9. The system of claim 1, further comprising an intrasaccular device configured to be implanted into the internal volume of the aneurysm.

10. The system of claim 1, wherein a size of the elongate lumen is no greater than 3 French.

11. A system for treating an aneurysm, the system comprising:
an elongate member comprising a lumen and a distal end portion configured to be positioned within an aneurysm; and
an injectable material comprising a biopolymer, and a chemical crosslinking agent, and a physical crosslinking agent, wherein the injectable material is configured to be delivered into the aneurysm via the lumen of the elongate member, and wherein the injectable material is configured to be delivered as a cohesive strand and to at least partially agglomerate to form a mass within the aneurysm.

12. The system of claim 11, wherein the biopolymer comprises chitosan or a derivative or an analog thereof.

13. The system of claim 11, wherein the chemical crosslinking agent comprises genipin or a derivative or an analog thereof.

14. The system of claim 11, wherein the physical crosslinking agent comprises β-glycerophosphate or a derivative or an analog thereof.

15. The system of claim 11, wherein the injectable material further comprises a contrast agent.

16. The system of claim 15, wherein the contrast agent comprises iohexol or a derivative or an analog thereof.

17. The system of claim 11, further comprising a syringe configured to deliver injectable material into the lumen of the elongate member.

18. The system of claim 17, wherein the syringe is configured to withstand a pressure of at least 500 psi to move the injectable material through the lumen to the aneurysm.

19. The system of claim 11, further comprising an intrasaccular device configured to be implanted into the aneurysm.

20. The system of claim 11, wherein a size of the lumen of the elongate member is no greater than 3 French.

* * * * *